US006534044B1

United States Patent
Wada et al.

(10) Patent No.: US 6,534,044 B1
(45) Date of Patent: Mar. 18, 2003

(54) COSMETIC PREPARATION, SURFACE-HYDROPHOBIZED SILICA-COATED METAL OXIDE PARTICLES, SOL OF SILICA-COATED METAL OXIDE, AND PROCESSES FOR PRODUCING THESE

(75) Inventors: Koichi Wada, Kawasaki (JP); Nobuaki Ishii, Kawasaki (JP); Mitsuharu Irie, Kawasaki (JP); Kazuo Sekiguchi, Kawasaki (JP); Michihiro Takama, Tokyo (JP)

(73) Assignee: Showa Denko K.K, Tokyo (JP)

( * ) Notice: Subject to any disclaimer, the term of this patent is extended or adjusted under 35 U.S.C. 154(b) by 0 days.

(21) Appl. No.: 09/889,048

(22) PCT Filed: Jan. 11, 2000

(86) PCT No.: PCT/JP00/00088

§ 371 (c)(1),
(2), (4) Date: Jul. 11, 2001

(87) PCT Pub. No.: WO00/42112

PCT Pub. Date: Jul. 20, 2000

Related U.S. Application Data

(60) Provisional application No. 60/117,551, filed on Jan. 28, 1999.

(30) Foreign Application Priority Data

| Jan. 11, 1999 | (JP) | 11-004613 |
| Nov. 2, 1999 | (JP) | 11-312318 |

(51) Int. Cl.⁷ ............................. A61K 7/42; A61K 7/00; C09C 1/36
(52) U.S. Cl. ..................... 424/59; 424/401; 106/436
(58) Field of Search .................... 424/401, 59; 106/436

(56) References Cited

U.S. PATENT DOCUMENTS

| 5,403,513 A | * | 4/1995 | Sato et al. ............... 106/286.4 |
| 5,587,148 A | * | 12/1996 | Mitchell et al. ............. 424/59 |
| 5,599,529 A | * | 2/1997 | Cowie ...................... 106/436 |
| 5,939,053 A | * | 8/1999 | Forestier et al. ........... 424/401 |
| 6,235,270 B1 | * | 5/2001 | Ishii et al. ................ 106/403 |

FOREIGN PATENT DOCUMENTS

| EP | 0 824 086 A1 | * | 2/1998 |
| JP | 60-226805 |   | 11/1985 |
| JP | 63-44519 |   | 2/1988 |
| JP | 3-115211 |   | 5/1991 |
| JP | 4-16518 |   | 1/1992 |
| JP | 6-192593 |   | 7/1994 |
| JP | 7-133105 |   | 5/1995 |
| JP | 7-315832 |   | 12/1995 |
| JP | 9-315939 |   | 12/1997 |
| JP | 10-158015 |   | 6/1998 |
| WO | 98/47476 |   | 10/1998 |

OTHER PUBLICATIONS

"The Physics and Chemistry of Sol–Gel Processing," C.J. Brinker, et al., SOL–GEL Science, pp. 580–583, Academic Press, Inc. 1990.
"Silic acid," Chemical Dictionary, pp. 300–303, 7th Printing, Kyoritsu Publishing, 1969.
"Funtai (Particles)," K. Kubo, et al., pp. 56–66, 1979.
"Cosmetic Material Standards, 2nd Edition, Annotated," edited by Nihon Koteisho Kyokai, pp. 26–35, Yakuji Nippo Publishing, 1984.
"Cosmetic Material Standards: Standardized Mixing Components," edited by Ministry of Health and Welfare, Pharmaceutical Affairs Dept., pp. 15–56, Yakuji Nippo Publishing, 1993.
"Supplementary Cosmetic Material Standards: Standardized Mixing Components," edited by Ministry of Health and Welfare, Pharmaceutical Affairs Dept., pp. 8–22 and 498, Yakuji Nippo Publishing, 1993.
"Cosmetic Classification and Approval Standards," edited by Ministry of Health and Welfare, Pharmaceutical Affairs Dept., Yakuji Nippo Publishing, 1990.
"Encyclopedia of Cosmetic Material Terms," Nikko Chemicals, pp. v–ix and 28, 1996.
"Titatnium Oxide—Properties and Application Techniques," M. Seino, pp. 196–197, Gihodo Publishing, 1991.
International Search Report, Mar. 30, 2000.

\* cited by examiner

*Primary Examiner*—Jose' S. Dees
*Assistant Examiner*—Marina Lamm
(74) *Attorney, Agent, or Firm*—Sughrue Mion, PLLC

(57) ABSTRACT

The invention relates to (1) a cosmetic material comprising silica-coated metal oxide particles further surface-treated with a hydrophobicizing agent, and (2) metal oxide particles having a specified infrared absorption spectrum intensity ratio and refractive index which are further treated with a hydrophobicizing agent, and to a process for their production. The invention further relates to a silica-coated metal oxide sol which gives such particles, and to a process for its production.

The invention can give ultraviolet-screening cosmetic materials with an excellent transparent feel, wherein the particles are satisfactorily dispersed.

30 Claims, No Drawings

COSMETIC PREPARATION, SURFACE-HYDROPHOBIZED SILICA-COATED METAL OXIDE PARTICLES, SOL OF SILICA-COATED METAL OXIDE, AND PROCESSES FOR PRODUCING THESE

CROSS REFERENCE TO RELATED APPLICATIONS

This application claims the advantage of a priority right based on U.S. Provisional Application No. 60/117551, filed on Jan. 28, 1999.

TECHNICAL FIELD

The present invention relates to a cosmetic material, to surface-hydrophobicized silica-coated metal oxide particles, to a silica-coated metal oxide sol and to a process for their production. More specifically, it relates to a cosmetic material and particularly an ultraviolet-screening cosmetic material, to surface-hydrophobicized silica-coated metal oxide particles suitable for use in the cosmetic material and to a process for their production, as well as to a silica-coated metal oxide sol suitable for use in a cosmetic material and particularly an ultraviolet-screening cosmetic material, having a specified infrared absorption spectrum peak, coated with a dense, practical silica film and having a small primary particle size with satisfactory dispersability. It further relates to a surface-hydrophobicized silica-coated metal oxide sol which is obtained by surface treatment with a hydrophobicizing agent after silica coating, and to a process for its production. Even more specifically, the present invention relates to a cosmetic material with an excellent feel during cosmetic use, a high ultraviolet-screening function, low phototoxicity and excellent storage stability, and to surface-hydrophobicized silica-coated metal oxide particles having a specified infrared absorption spectrum peak, coated with a dense, practical silica film and being surface treated with a hydrophobicizing agent, the surface-hydrophobicized silica-coated metal oxide particles being suited for use as ultraviolet-screening materials, cosmetic products, pigments and the like. The invention still further relates to a cosmetic material containing the silica-coated metal oxide sol and/or surface-hydrophobicized silica-coated metal oxide sol, exhibiting a high ultraviolet-screening function, a high photocatalytic activity-suppressing effect, excellent storage stability and excellent feel and transparency for cosmetic use.

BACKGROUND ART

Many of the ultraviolet-screening cosmetic materials used in recent years have been inorganic-based ultraviolet-screening materials with excellent ultraviolet-screening function and high stability. Such commonly used inorganic-based ultraviolet-screening materials include metal oxide powders of titania and zinc oxide.

When these metal oxide powders are added directly to cosmetic materials, however, problems are known to occur such as a poor feel or adverse effect on the human body or skin due to the photocatalytic activity of the metal oxide particles, and it has therefore been necessary to provide the metal oxide particles with some manner of coating. A coating of an inorganic substance is particularly preferred because it is resistant to chemical change by photocatalytic reaction.

However, although inorganic-coated metal oxide particles have a photocatalytic activity-suppressing effect when added to cosmetic materials, they have been inconvenient in that their dispersion in hydrophobic base materials is insufficient and excellent powder properties are not adequately exhibited, when incorporated into oily cosmetic materials, W/O dispersion cosmetic materials or water-repellent cosmetic materials that are resistant to cosmetic disintegration due to perspiration and moisture.

Also, when particles of a metal oxide such as titania or zinc oxide, which are widely used as highly stable inorganic ultraviolet-screening materials with the excellent ultraviolet-screening function described above, are added directly to cosmetic materials, it is common to coat the surfaces with an inorganic substance with no photocatalytic activity, because of the problems of poor feel during cosmetic use or adverse effect on the human body due to the photocatalytic activity of the metal oxide particles. Metal oxide particles coated with alumina, silica and the like are commercially available, but no product has been known which satisfies both aspects of suppressing the photocatalytic activity by the coating and improving the feel, during use, when added to cosmetics.

The present inventors have disclosed silica-coated metal oxide particles having a silica film wherein the ratio I of the peak intensities of the infrared absorption spectrum at 1150–1250 $cm^{-1}$ and 1003–1100 $cm^{-1}$ (I=I1/I2: where I1 is the maximum absorption peak intensity in the range of 1150–1250 $cm^{-1}$ and I2 is the maximum absorption peak intensity in the range of 1000–1100 $cm^{-1}$) is 0.2 or greater, and the refractive index is 1.435 or greater, a process for their production and a cosmetic material comprising them, and have demonstrated that an ultraviolet-screening cosmetic material with a satisfactory feel during use, a high suppressing effect on photocatalytic activity and excellent storage stability can be obtained by including these silica-coated metal oxide particles coated with a silica film of a thickness between 0.1 and 100 nm and having photocatalytic activity of no more than 60 Pa/min as measured by the tetralin autooxidation method (PCT/JP98/01133).

In recent years, ultraviolet-screening cosmetic materials have needed a satisfactory feel during use and a highly transparent feel or appearance, in addition to the high ultraviolet-screening function. In order to provide a satisfactory feel in use, and a transparent feel or appearance for the metal oxide particles added to cosmetic materials as ultraviolet-screening materials, it has become more desirable to decrease the size of the primary particles and improve the dispersion properties. The aforementioned silica-coated metal oxide particles based on the invention of the present inventors have excellent properties such as suppression of photocatalytic activity and an excellent feel during use, but further improvement in the particle fineness and dispersion properties have been desired to increase the transparency when added to cosmetic materials.

However, because metal oxide powders with small primary particle sizes produce lumps when suspended in solvents, they do not readily undergo high dispersion and require extra steps such as the use of ultrasonic waves for silica coating or prolonged stirring, which constitutes a problem in economic terms.

It is a first object of the present invention to provide a cosmetic material with satisfactory dispersion of metal oxide particles in an oily base, an excellent feel during cosmetic use, a high ultraviolet-screening function, low phototoxicity and excellent storage stability, and to provide surface-hydrophobicized silica-coated metal oxide particles coated with a dense, practical silica film having specific properties and a high contouring property, as well as an economical method for the production thereof.

It is a second object of the invention to provide an economical production method for the above-mentioned silica-coated metal oxide sol, to provide a metal oxide sol coated with a dense, practical silica film to exhibit improved dispersion properties and transparency, and to provide an ultraviolet-screening cosmetic material with a particularly excellent transparent feel or appearance, wherein the silica-coated metal oxide disperses satisfactorily in the cosmetic material.

DISCLOSURE OF THE INVENTION

The present invention which achieves the two aforementioned objects is as follows. Aspects (1) to (21) relate particularly to the first object, while aspects (22) to (48) relate particularly to the second object.

(1) A cosmetic material characterized by comprising surface-hydrophobicized silica-coated metal oxide particles obtained by further treating the surface of silica-coated metal oxide particles with a hydrophobicizing agent.

(2) A cosmetic material comprising surface-hydrophobicized silica-coated metal oxide particles according to (1) above, characterized in that the silica film thickness is 0.1–100 nm.

(3) A cosmetic material according to (1) or (2) above, characterized in that the hydrophobicizing agent is one or more hydrophobicizing agents selected from the group consisting of silicone oils, organic alkoxysilanes and higher fatty acid salts.

(4) A cosmetic material according to any one of (1) to (3) above, characterized by comprising surface-hydrophobicized silica-coated metal oxide particles with a photocatalytic activity of no more than 60 Pa/min as measured by the tetralin autooxidation method.

(5) A cosmetic material according to (3) above, characterized in that the surface-hydrophobicized silica-coated metal oxide particles have a primary particle size of 5–500 nm and a secondary particle size of 0.5–10 μm.

(6) A cosmetic material according to any one of (1) to (5) above, characterized in that the primary particle size of the surface-hydrophobicized silica-coated metal oxide particles is 5–120 nm and the silica film thickness is 0.5–25 nm.

(7) A cosmetic material according to any one of (1) to (6) above, characterized in that the metal oxide is one or more metal oxides selected from the group consisting of titanium oxide, zinc oxide, cerium oxide, zirconium oxide and iron oxide.

(8) A cosmetic material according to (7) above, wherein the metal oxide is titanium oxide.

(9) A cosmetic material according to (7) above, wherein the metal oxide is zinc oxide.

(10) A cosmetic material according to (7) above, wherein the metal oxide is cerium oxide.

(11) A cosmetic material according to any one of (1) to (10) above, characterized by comprising an antioxidant in addition to the surface-hydrophobicized silica-coated metal oxide particles.

(12) A cosmetic material according to any one of (1) to (11) above, characterized by comprising an organic-based ultraviolet absorber in addition to the surface-hydrophobicized silica-coated metal oxide particles.

(13) Surface-hydrophobicized silica-coated metal oxide particles characterized by being obtained by using a hydrophobicizing agent for further surface treatment of metal oxide particles coated with a silica film wherein the ratio I of the absorption peak intensities of the infrared absorption spectrum at 1150–1250 cm$^{-1}$ and 1000–1100 cm$^{-1}$ (I=I$_1$/I$_2$: where I$_1$ is the absorption peak intensity at 1150–1250 cm$^{-1}$ and I$_2$ is the absorption peak intensity at 1000–1100 cm$^{-1}$) is 0.2 or more, and the refractive index is 1.435 or more.

(14) Surface-hydrophobicized silica-coated metal oxide particles according to (13) above, characterized in that the hydrophobicizing agent is one or more hydrophobicizing agents selected from the group consisting of silicone oils, organic alkoxysilanes and higher fatty acid salts.

(15) Surface-hydrophobicized silica-coated metal oxide particles according to (13) or (14) above, characterized in that the average primary particle size of the metal oxide particles is 5–500 nm.

(16) A process for producing surface-hydrophobicized silica-coated metal oxide particles, characterized by using a hydrophobicizing agent for further surface treatment of silica-coated metal oxide particles obtained by contacting metal oxide particles with a silica coating-forming composition containing a) silicic acid or a silicic acid-producing precursor, b) water, c) an alkali and d) an organic solvent, with a water/organic solvent ratio in the range of 0.1–10 and a silicon content in the range of 0.0001–5 moles/liter to selectively deposit silica on the surface of the metal oxide particles.

(17) A process for producing surface-hydrophobicized silica-coated metal oxide particles according to (16) above, characterized in that the hydrophobicizing agent used for the hydrophobicizing agent surface treatment is one or more hydrophobicizing agents selected from the group consisting of silicone oils, organic alkoxysilanes and higher fatty acids.

(18) A process for producing surface-hydrophobicized silica-coated metal oxide particles according to (16) or (17) above, characterized in that the hydrophobicizing agent is an alkylalkoxysilane represented by the following formula [1]:

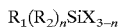   Formula [1]

where R$_1$ is an alkyl group of 1–3 carbons or phenyl, R$_2$ is a hydrogen atom, alkyl group of 1–3 carbons or phenyl, X is an alkoxyl group of 1–4 carbons and n is an integer of 1–2.

(19) A process for producing surface-hydrophobicized silica-coated metal oxide particles according to any one of (16) to (18) above, which is a process for production of surface-hydrophobicized silica-coated metal oxide particles wherein an alkylalkoxysilane is used for further surface treatment of silica-coated metal oxide particles obtained by contacting metal oxide particles with a silica coating-forming composition containing silicic acid or a silicic acid-producing precursor, water, an alkali and an organic solvent, with a water/organic solvent ratio in the range of 0.1–10 and a silicon content in the range of 0.0001–5 moles/liter to selectively deposit silica on the surface of the metal oxide particles, the procedure being characterized in that after contacting metal oxide particles with a silica coating forming composition containing silicic acid or a silicic acid-producing precursor, water, an alkali and an organic solvent, with a water/organic solvent ratio in the range of 0.1–10 and a silicon content in the range of 0.0001–5 moles/liter to selectively deposit silica on the surface of the metal oxide particles, the alkylalkoxysilane is added to make a composition with a water/organic solvent ratio in the range of 0.1–10 and a silicon content in the range of 0.0001–5 moles/liter derived from the alkylalkoxysilane, and the silica-coated metal oxide particles are surface treated with the reaction product of the alkylalkoxysilane, to continuously accomplish surface treatment with the silica coating and alkylalkoxysilane.

(20) A process for producing surface-hydrophobicized silica-coated metal oxide particles according to any one of (16) to (19) above, characterized in that the alkali is at least one selected from among ammonia, ammonium carbonate, ammonium bicarbonate, ammonium formate and ammonium acetate.

(21) A process for producing surface-hydrophobicized silica-coated metal oxide particles according to (16) above, characterized in that the organic solvent is at least one selected from among methanol, ethanol, propanol, pentanol, tetrahydrofuran, 1,4-dioxane and acetone.

(22) A process for producing a silica-coated metal oxide sol, characterized by combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0,0001–5 moles/liter after combining, and depositing silica on the surface of the metal oxide sol particles to form a silica film.

(23) A process for producing a silica-coated metal oxide sol according to (22) above, characterized by adding (d) a metal oxide sol produced by hydrolysis to a mixture of a) an alkali, b) an organic solvent and c) water, and then further adding a mixture comprising e) silicic acid or a silicic acid-producing precursor, f) an organic solvent and if necessary, g) water, for a water/organic solvent ratio in the range of 0.1–10 and a silicon content in the range of 0.0001–5 moles/liter after addition, and depositing silica on the surface of the metal oxide sol particles to form a silica film.

(24) A process for producing a silica-coated metal oxide sol according to (22) or (23) above, characterized in that the alkali is at least one selected from among ammonia, ammonium carbonate, ammonium bicarbonate, ammonium formate and ammonium acetate.

(25) A process for producing a silica-coated metal oxide sol according to any one of (22) to (24) above, characterized in that the organic solvent is at least one selected from among methanol, ethanol, propanol, pentanol, tetrahydrofuran, 1,4-dioxane and acetone.

(26) A silica-coated metal oxide sol, obtained by a process for producing a silica-coated metal oxide sol characterized by combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0.0001–5 moles/liter after combining, and depositing silica on the surface of the metal oxide sol particles to form a silica film.

(27) A silica-coated metal oxide sol, obtained by a process for producing a silica-coated metal oxide sol characterized by adding (d) a metal oxide sol produced by hydrolysis to a mixture of a) an alkali, b) an organic solvent and c) water, and then further adding a mixture comprising e) silicic acid or a silicic acid-producing precursor, f) an organic solvent and if necessary, g) water, for a water/organic solvent ratio in the range of 0.1–10 and a silicon content in the range of 0.0001–5 moles/liter after addition, and depositing silica on the surface of the metal oxide sol particles to form a silica film.

(28) A silica-coated metal oxide sol according to (26) or (27) above, characterized in that for the silica film, the ratio I of the absorption peak intensities of the infrared absorption spectrum at 1150–1250 cm$^{-1}$ and 1000–1100 cm$^{-1}$ (I=I$_1$/I$_2$: where I$_1$ is the maximum absorption peak intensity at 1150–1250 cm$^{-1}$ and I$_2$ is the maximum absorption peak intensity at 1000–1100 cm$^{-1}$ ) is 0.2 or more, and the refractive index is 1.435 or more.

(29) A silica-coated metal oxide sol according to any one of (26) to (28) above, characterized in that the thickness of the silica film coating the surface of the metal oxide particles is 0.1–25 nm.

(30) A silica-coated metal oxide sol according to any one of (26) to (29) above, characterized in that the average primary particle size of the metal oxide particles is 1–100 nm.

(31) A process for producing a surface-hydrophobicized silica-coated metal oxide sol, characterized by combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent.

(32) A process for producing a surface-hydrophobicized silica-coated metal oxide sol, characterized by adding (d) a metal oxide sol produced by hydrolysis to a mixture of a) an alkali, b) an organic solvent and c) water, and then further adding a mixture comprising e) silicic acid or a silicic acid-producing precursor, f) an organic solvent and if necessary, g) water, for a water/organic solvent ratio in the range of 0.1–10 and a silicon content in the range of 0.0001–5 moles/liter after addition, and depositing silica on the surface of the metal oxide sol particles to form a silica film, thereby fabricating a silica-coated metal oxide sol, and then further surface treating the silica-coated metal oxide particles with a hydrophobicizing agent.

(33) A process for producing a surface-hydrophobicized silica-coated metal oxide sol according to (31) or (32) above, characterized in that the hydrophobicizing agent is one or more hydrophobicizing agents selected from the group consisting of silicone oils, organic alkoxysilanes and higher fatty acid salts.

(34) A process for producing a surface-hydrophobicized silica-coated metal oxide sol according to any one of (31) to (33) above, characterized in that the organic alkoxysilane is an alkylalkoxysilane represented by the following structural formula:

$$R_1(R_2)_n SiX_{3-n}$$

where R$_1$ is an alkyl group of 1–4 carbons or phenyl, R$_2$ is a hydrogen atom, an alkyl group of 1–4 carbons or phenyl, X is an alkoxyl group of 1–4 carbons and n is an integer of 0–2.

(35) A surface-hydrophobicized silica-coated metal oxide sol obtained by a process for production of a surface-hydrophobicized silica-coated metal oxide sol which comprises combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent.

(36) A surface-hydrophobicized silica-coated metal oxide sol according to (35) above, characterized in that for the silica film, the ratio I of the absorption peak intensities of the infrared absorption spectrum at 1150–1250 cm$^{-1}$ and 1000–1100 cm$^{-1}$ (I=I$_1$/I$_2$: where I$_1$ is the maximum absorption peak intensity at 1150–1250 cm$^{-1}$ and I$_2$ is the maximum absorption peak intensity at 1000–1100 cm$^{-1}$) is 0.2 or greater, and the refractive index is 1.435 or greater.

(37) A surface-hydrophobicized silica-coated metal oxide sol according to (35) or (36) above, characterized in that the thickness of the silica film coating the surface of the metal oxide particles is 0.1–25 nm.

(38) A surface-hydrophobicized silica-coated metal oxide sol according to any one of (35) to (37) above, 3,0 characterized in that the average primary particle size of the metal oxide particles is 1–100 nm.

(39) Silica-coated metal oxide sol-derived silica-coated metal oxide particles obtained by solid/liquid separation, drying and if necessary pulverization of a silica-coated metal oxide sol obtained by a process for production of a silica-coated metal oxide sol characterized by combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0.0001–5 moles/liter after combining, and depositing silica on the surface of the metal oxide sol particles to form a silica film.

(40) Surface-hydrophobicized silica-coated metal oxide sol-derived surface-hydrophobicized silica-coated metal oxide particles obtained by solid/liquid separation, drying and if necessary pulverization of a surface-hydrophobicized silica-coated metal oxide sol obtained by a process for production of a surface-hydrophobicized silica-coated metal oxide sol characterized by combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent.

(41) A cosmetic material characterized by comprising a silica-coated metal oxide sol obtained by a process for production of a silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, and/or a surface-hydrophobicized silica-coated metal oxide sol obtained by a process for production of a surface-hydrophobicized silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent.

(42) A cosmetic material characterized by comprising silica-coated metal oxide particles obtained by solid/liquid separation, drying and, if necessary, pulverization of a silica-coated metal oxide sol which are obtained by a process for production of a silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, and/or surface-hydrophobicized silica-coated metal oxide particles obtained by solid/liquid separation, drying and if necessary pulverization of a surface-hydrophobicized silica-coated metal oxide sol obtained by a process for production of a surface-hydrophobicized silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent.

(43) A cosmetic material according to (41) or (42) above, characterized in that the thickness of the silica film of the metal oxide particles in the silica-coated metal oxide sol and surface-hydrophobicized silica-coated metal oxide sol is 0.1–25 nm.

(44) A cosmetic material according to any one of (41) to (43) above, characterized in that the average primary particle size of the metal oxide particles in the silica-coated metal oxide sol and surface-hydrophobicized silica-coated metal oxide sol is 1–100 nm.

(45) A cosmetic material according to any one of (41) to (44) above, characterized in that the photocatalytic activity of the metal oxide particles in the silica-coated metal oxide sol and surface-hydrophobicized silica-coated metal oxide sol is no more than 60 Pa/min as measured by the tetralin autooxidation method.

(46) A cosmetic material according to any one of (41) to (45) above, characterized in that the metal oxide is one or more metal oxides selected from the group consisting of titanium oxide, zinc oxide, cerium oxide, zirconium oxide and iron oxide.

(47) A cosmetic material according to any one of (41) to (46) above, characterized by comprising an antioxidant.

(48) A cosmetic material according to any one of (41) to (47) above, characterized by comprising an organic-based ultraviolet absorber.

The term "dense" according to the present invention means that the refractive index of the formed silica film is 1.435 or greater. The density of a silica film and its refractive index are generally considered to have a positive correlation (see, for example, C. JEFFEREY BRINKER, Saul—GEL SCIENCE, 581–583, ACADEMIC PRESS (1990)), and although silica films obtained by ordinary sol-gel methods have a refractive index of 1.435 or greater if firing is carried out, the density is low at below 1.435 in the absence of firing. According to the present invention, however, this value is achieved without firing.

Also, the term practical according to the invention means that the silica has strong covering power on the metal oxide base, with substantially no peeling of the coating, and with an adequate degree of hydrophilicity.

The hydrophilicity of the silica film is expressed as the ratio I of the peak intensities of the infrared absorption spectrum at 1150–1250 cm$^{-1}$ and 1000–1100 cm$^{-1}$ (I=$I_1/I_2$: where $I_1$ is the maximum absorption peak intensity in the range of 1150–1250 cm$^{-1}$ and $I_2$ is the maximum absorption peak intensity in the range of 1000–1100 cm$^{-1}$). In other words, $I_1$ is the absorption by deformation vibration of SiOH, $I_2$ is the absorption due to stretching vibration of Si—O—Si, and a larger $I_1/I_2$ represents higher hydrophilicity. The phrase "adequate degree of hydrophilicity" according to the invention means that the value is at least 0.2. Silica films obtained by ordinary sol-gel methods have an I value of 0.2 or greater without firing, but the density is lower, as explained above. On the other hand, although the density is improved by firing, the I value falls below 0.2 representing lower hydrophilicity which is no longer adequate. A silica coating according to the invention, however, has adequate hydrophilicity to maintain satisfactory surface properties (moistness, smoothness) when added to cosmetic materials, while also serving as a dense, firm coating that has been unachievable in the past without firing, so that it is possible to maintain high suppression of the photocatalytic activity of the metal oxide even with a very thin film thickness of about 0.1 nm.

Best Mode for Carrying Out the Invention

The present invention will now be explained in further detail.

(Introduction)

First, according to one aspect of the invention, the cosmetic material comprises surface-hydrophobicized coated metal oxide particles that have been surface treated with a hydrophobicizing agent. The surface-hydrophobicized coated metal oxide particles are sufficiently effective so long as the surfaces are hydrophobicized. The present inventors found that a cosmetic material with the desired properties can be obtained by adding surface-hydrophobicized silica-coated metal oxide particles prepared by coating metal oxide particles with a silica film and further hydrophobicizing their surfaces.

The metal oxide particles used, however, preferably are coated with a silica film wherein the ratio I of the peak intensities of the infrared absorption spectrum at 1150–1250 cm$^{-1}$ and 1000–1100 cm$^{-1}$ (I=$I_1/I_2$: where $I_1$ is the absorption peak intensity in the range of 1150–1250 cm$^{-1}$ and $I_2$ is the absorption peak intensity in the range of 1000–1100 cm$^{-1}$) is 0.2 or greater and the refractive index is 1.435 or greater, and the metal oxide particles are further surface treated with a hydrophobicizing agent to obtain surface-hydrophobicized silica-coated metal oxide particles.

Such suitable surface-hydrophobicized silica-coated metal oxide particles can be obtained by contacting metal oxide particles with a silica coating-forming composition containing a) silicic acid or a silicic acid-producing precursor, b) water, c) an alkali and d) an organic solvent, with a water/organic solvent ratio in the range of 0.1–10 and a silicon content in the range of 0.0001–5 moles/liter to selectively deposit silica on the surface of the metal oxide particles, and then further surface treating the resulting silica-coated metal oxide particles with a hydrophobicizing agent.

The present invention will now be explained with particular focus on this preferred process for producing surface-hydrophobicized silica-coated metal oxide particles, and the explanation will be accompanied by an explanation of silica coating of a metal oxide sol without hydrophobicizing treatment of silica-coated metal oxide particles, according to a second aspect of the invention.

According to the second aspect of the invention, a silica-coated metal oxide sol is produced by a process wherein metal oxide particles are contacted with a silica coating-forming composition containing silicic acid or a silicic acid-forming precursor, water, an alkali and an organic solvent, with a water/organic solvent ratio in the range of 0.1–10 in terms of volume ratio and a silicon content in the range of 0.0001–5 moles/liter, by which silica is selectively deposited on the surface of the metal oxide particles, wherein the metal oxide sol produced by hydrolysis in the silica coating-forming composition is used for the metal oxide particles. That is, the process for producing a silica-coated metal oxide sol is characterized by combining a) a metal oxide sol produced by hydrolysis, b) silicic acid or a silicic acid-producing precursor, c) an alkali, d) an organic solvent and if necessary, e) water, irrespective of order, for a water/organic solvent ratio in the range of 0.1–10 and a silicon content in the range of 0.0001–5 moles/liter after combining, and depositing silica on the surface of the metal oxide sol particles to form a silica film.

According to the second aspect of the invention, the resulting silica-coated metal oxide sol may be also be subjected to surface hydrophobicizing treatment.

The silica-coated metal oxide sol according to the second aspect of the invention is produced using a metal oxide sol as the starting material, by solution treatment alone without a drying step and, therefore, since the satisfactory dispersability and the small primary particle size of the starting sol are retained, it is possible to obtain a cosmetic material with a more transparent feel. It is also economical because of its large surface area, its high ultraviolet-screening function per unit mass and its effect by a less amount of addition. The invention also encompasses surface-hydrophobicized silica-coated metal oxide sols obtained by surface treatment of silica-coated metal oxide fine particles in the aforementioned silica-coated metal oxide sol with a hydrophobicizing agent. Such sols are suitable when incorporated into oily-based cosmetic materials, W/O dispersion-type cosmetic materials or water-repellent cosmetic materials that are resistant to cosmetic disintegration by perspiration and moisture. Such silica-coated sols or surface-hydrophobicized silica-coated sols have been hitherto unknown.

(Silicic Acid)

According to the invention, the silicic acid used in the silica coating-forming composition is ortho-silicic acid or one of its polymers, meta-silicic acid, meso-silicic acid, meso-trisilicic acid, meso-tetrasilicic acid, etc., as described, for example, under "Silicic acid" in Kagaku Daijiten (Chemical Dictionary, 7th Printing, Mar. 15, 1969, Kyoritsu Publishing). It is important that such "silicic acid" should contain no organic groups or halogen groups.

A composition containing the silicic acid can be obtained, for example, by adding water, an alkali and an organic solvent to a tetraalkoxysilane (Si(OR)$_4$, where R is a hydrocarbon group, and specifically tetramethoxysilane, tetraethoxysilane, tetra-n-propoxysilane, tetraisopropoxysilane, tetra-n-butoxysilane or the like) and stirring the mixture to promote hydrolysis reaction. This process is preferred because of its practicality and ease of handling and operation. Tetraethoxysilane is the preferred material.

A composition containing silicic acid may also be obtained using a method of adding water, an alkali and an organic solvent to a tetrahalogenated silane for hydrolysis, a method of adding an alkali and organic solvent to water-glass, or a method of treating water-glass with an cationic exchange resin and adding an alkali and organic solvent. The tetraalkoxysilane, tetrahalogenated silane and water-glass used as the starting materials for the silicic acid are not particularly restricted and may be any ones employed industrially or in common use as reagents; however, they are preferably of high purity. The silica coating-forming composition in this composition may also contain unreacted components of the silicic acid starting material.

The amount of silicic acid is not particularly restricted, but is preferably in the range of 0.0001–5 moles/liter in terms of silicon content. If the silicon content is less than 0.0001 mole/liter, the silica coating formation rate is drastically slowed to an impractical extent. If it exceeds 5 moles/liter, silica particles are sometimes produced in the composition without forming a coating.

The silicon content can be calculated from the amount of silicic acid starting material, such as tetraethoxysilane, which is added, but it may also be measured by atomic absorption spectrophotometry of the composition. The measurement may be carried out using the silicon spectrum wavelength of 251.6 nm as the analytical line, and a frame made of acetylene/nitrous oxide.

(Water)

The water used in the silica coating-forming composition is not particularly restricted, but is preferably water from which the particles have been removed by filtration or the like. When particles are present in the water, undesirable impurities are included in the product.

The water is preferably used in an amount in the range of 0.1–10 in terms of the volume ratio of water/organic solvent. Outside of this range, a film may not be formable, or the film-forming rate may be radically reduced. The water/organic solvent volume ratio is more preferably in the range of 0.1–0.5. The type of alkali used is not limited if the water/organic solvent ratio is in the range of 0.1–0.5. When the ratio is outside of this range, i.e. with a water/organic solvent ratio of greater than 0.5, non-alkali-metal alkalis such as ammonia, ammonium bicarbonate and ammonium carbonate are preferred for formation of the film.

(Alkali)

The alkali used for the silica coating-forming composition is not particularly restricted, and there may be used, for example, inorganic alkalis such as ammonia, sodium hydroxide and potassium hydroxide, inorganic alkali salts such as ammonium carbonate, ammonium bicarbonate, sodium carbonate and sodium bicarbonate, organic alkalis such as monomethylamine, dimethylamine, trimethylamine, monoethylamine, diethylamine, triethylamine, pyridine, aniline, choline, tetramethylammonium hydroxide and guanidine, and organic acid alkali salts such as ammonium formate, ammonium acetate, monomethylamine formate, dimethylamine acetate, pyridine lactate, guanidinoacetic acid and aniline acetate. Among these, ammonia, ammonium carbonate, ammonium bicarbonate, ammonium formate, ammonium acetate, sodium carbonate and sodium bicarbonate are particularly preferred. The alkali used may be any one of these or two or more thereof in combination.

There are no particular restrictions on the purity of the alkali used for the composition, and any employed industrially or in common use as reagents may be used; however, they are preferably of high purity.

Raising the temperature during the coating formation is effective to increase the film formation rate. In such cases it is preferred to use an alkali and an organic solvent which do not easily vaporize and decompose at the coating-forming temperature.

A film can still be formed if the alkali is added in a trace amount such as 0.002 mole/liter in the case of sodium carbonate, for example, but it may also be added in a larger amount of about 1 mole/liter. However, a solid alkali is preferably not added in an amount exceeding its solubility, because it will be included as an impurity in the metal oxide particles.

By using an alkali with no alkali metal as the major component, it is possible to prepare silica-coated metal oxide particles with a low alkali metal content. Particularly preferred are ammonia, ammonium carbonate and ammonium bicarbonate because of their film-forming rate and easy residue removal.

(Organic Solvent)

The organic solvent used in the coating-forming composition is preferably one in which the composition forms a uniform solution. For example, there may be used alcohols such as methanol, ethanol, propanol and pentanol, ethers and acetals such as tetrahydrofuran and 1,4-dioxane, aldehydes such as acetaldehyde, ketones such as acetone, diacetone alcohol and methyl ethyl ketone, and polyhydric alcohol derivatives such as ethylene glycol, propylene glycol and diethylene glycol. Alcohols are particularly preferred among these, with ethanol being especially preferred. Any one or a combination of two or more selected from this group may be used as the organic solvent.

There are no particular restrictions on the purity of the organic solvent used for the composition, and any solvents that are employed industrially or in common use as reagents may be used; however, they are preferably of high purity.

(Silica Coating-forming Composition)

A common solution preparation method may be applied for preparation of the silica coating-forming Composition. One possible method is addition of prescribed amounts of the alkali and water to the organic solvent and stirring, followed by addition of tetraethoxysilane and stirring, but a coating may be formed with the components combined in any order. When the water and tetraethoxysilane are combined, it is preferred for both to be diluted with the organic solvent, for better control of the reaction.

A silica coating-forming composition prepared in this manner, satisfying the conditions of comprising silicic acid or a silicic acid-forming precursor, c) an alkali and d) an organic solvent, wherein the water/organic solvent ratio is in the range of 0.1–10 and the silicon content is in the range of 0.0001–5 moles/liter, is a stable composition that undergoes substantially no sedimentation or deposition prior to contact with the metal oxide particles. After contacting the metal oxide particles with the composition, silica begins to be selectively deposited on the surfaces of the metal oxide particles. Selective deposition of silica on the surfaces of the metal oxide particles according to the invention means that when the metal oxide particles are in a state of contact with the silica coating-forming composition, the actual liquid of the silica coating-forming composition is stable and undergoes substantially no sedimentation or deposition (i.e. silica precipitation) and is therefore transparent, but that silica selectively precipitates from the liquid composition only at the sites of contact with the surfaces of the metal oxide particles, forming a solid silica coating at those sites. In other words, it is not the case that after the solid silica (in the form of particles, etc.) has been produced in the liquid of the silica coating-forming composition, the solid silica move or accumulate (adhere) to the surfaces of the metal oxide particles, or the solid silica adheres to the surfaces of the metal oxide particles by drying of the gel of the silica coating-forming composition which has produced the solid silica.

The contact between the silica coating-forming composition and the metal oxide particles may be accomplished after preparation of the silica coating-forming composition which satisfies the above-mentioned conditions, or else a portion of the silica coating-forming composition components may be placed in contact with the metal oxide particles and the remaining components of the silica coating-forming composition added thereafter, to prepare the silica coating-forming composition which satisfies the above-mentioned conditions. Regardless of the method, preparation of a composition satisfying the conditions of the invention can prevent sedimentation or deposition of the silica coating-forming composition or any of its components (i.e. precipitation of silica) at all but the sections of contact with the metal oxide particles.

(Metal Oxide)

The metal oxide as a starting material for the silica-coated metal oxide particles of the invention (Throughout the present specification, a reference simply to silica-coated metal oxide particles will as a rule include the silica-coated metal oxide particles composing the silica-coated metal oxide sol according to the second aspect of the invention, or the silica-coated metal oxide particles obtained from the silica-coated metal oxide sol, and special note will be made when it is necessary to specifically explain the silica-coated metal oxide sol.) is preferably one or more metal oxides selected from the group consisting of titania, zinc oxide, cerium oxide, zirconium oxide and iron oxide. There are no particular restrictions on the process for producing the metal oxide particles used as the starting material, and any method may be employed. In the case of titania powder, for example, it may be produced by any production method such as high-temperature vapor-phase oxidation of $TiCl_4$, vapor-phase hydrolysis of $TiCl_4$, the sulfuric acid method, the chlorine method, etc.

The crystallinity of the metal oxide may be of any crystal form. In the case of titania, for example, it may be amorphous, rutile, anatase or buchite, or a mixture thereof. However, the metal oxide particles preferably have a minimum of impurities, and preferably a low degree of aggregation for better control of the secondary particle size.

(Silica-coated Metal Oxide Sol-forming Composition)

A common solution preparation method may also be employed to prepare the silica-forming composition used to produce the silica-coated metal oxide sol of the invention. One possible method, for example, is adding the alkali, water and organic solvent to a prescribed amount of the metal oxide sol, stirring for thorough dispersion of the metal oxide sol, and then adding tetraethoxysilane and stirring; however, a coating can be formed with any order of combination and with any number of repeated additions. When the water and tetraethoxysilane are combined, it is preferred for both to be diluted with the organic solvent, for better control of the reaction.

A silica coating-forming composition prepared in this manner is a stable composition, as the composition described above, that undergoes substantially no sedimentation or deposition prior to contact with the metal oxide sol so long as it satisfies the same conditions described above. After contacting the metal oxide sol with the composition, silica begins to be selectively deposited on the surfaces of the metal oxide sol.

The dispersion of the metal oxide sol obtained by the process described above may be used for the silica coating-forming composition either in its direct state, or if necessary after removal of the unreacted substances, adjustment of the pH, or administration of the concentrations of the metal oxide sol, water and organic solvent. The crystallinity of the metal oxide sol may be of any crystal form. In the case of a titania sol, for example, it may be amorphous, rutile, anatase or buchite, or any mixture thereof. However, the metal oxide sol preferably has a minimum of impurities, and preferably a low degree of aggregation n order to achieve the object of the invention. A metal oxide sol with a low degree of aggregation can be obtained by suitably adjusting the electrolytes and the pH conditions. The average primary particle size of the metal oxide fine particles composing the metal oxide sol is preferably 1–100 nm, and more preferably 5–20 nm. The average primary particle size can be controlled by suitably adjusting the reaction conditions including the temperature, concentration, firing time, etc.

According to the invention, there is used a silica-coated metal oxide sol in which the surfaces of the oxide particles in the sol are coated with a silica film wherein the ratio I of the absorption peak intensities of the infrared absorption spectrum at 1150–1250 $cm^{-1}$ and 1000–1100 $cm^{-1}$ ($I=I_1/I_2$: where $I_1$ is the maximum absorption peak intensity at 1150–1250 $cm^{-1}$ and $I_2$ is the maximum absorption peak intensity at 1000–1100 $cm^{-1}$) is 0.2 or greater, and the refractive index is 1.435 or greater.

The aforementioned silica-coated metal oxide sol which may be used in a cosmetic material according to the invention is obtained by a process whereby silicic acid or a silicic acid-producing precursor, an alkali, an organic solvent and if necessary water, are added to a metal oxide sol produced by hydrolysis to a water/organic solvent ratio in the range of 0.1–10 and a silicon content in the range of 0.0001–5 moles/liter after addition, and silica is deposited on the surface of the metal oxide sol to form a silica film.

More preferably, it is obtained by a process whereby a metal oxide sol produced by hydrolysis is added to a mixture comprising an alkali, an organic solvent and if necessary water, and then a mixture comprising silicic acid or a silicic acid-producing precursor, an organic solvent and if necessary water is further added to a water/organic solvent ratio in the range of 0.1–10 and a silicon content in the range of 0.0001–5 moles/liter after addition, and silica is deposited on the surface of the metal oxide sol particles to form a silica film.

The metal oxide sol serving as the starting material for the silica-coated metal oxide sol may comprise as the metal oxide, any one, or more than one, selected from the group consisting of titanium oxide, zinc oxide, cerium oxide, zirconium oxide and iron oxide.

The process for producing the metal oxide sol is not particularly restricted, and the sol used may be produced by any process, for example, a process in which an alkoxide, an acetylacetonate, an organic salt such as an acetate or oxalate, or an inorganic compound such as a chloride, oxychloride or nitrate of a metal element is hydrolyzed. It is preferably produced by a process of hydrolysis of a metal alkoxide or metal chloride.

(Silica Coating-forming Method)

Basically, a silica film may be formed by immersing the metal oxide particles in the silica coating-forming composition and holding it at a prescribed temperature to selectively deposit the silica on the surface of the metal oxide. The coating-forming composition may also be prepared in advance and the metal oxide particles loaded therein to form the silica film, or the metal oxide particles may be suspended in a solvent in advance and then the other starting components added to prepare the coating-forming composition for formation of the silica film. In other words, there are no particular restrictions on the order of loading the starting materials for the coating-forming composition or the metal oxide particles, as the coating can be formed with an order of addition.

Of these methods, preparation of a suspension with the metal oxide particles, organic solvent, water and alkali and then periodic loading of a tetraalkoxysilane diluted with the organic solvent is preferred because it can form a dense, satisfactory silica film, and an industrially useful continuous process can be constructed. Even when a metal oxide sol is used, addition of the metal oxide sol to a mixture of the organic solvent, water and alkali and then periodic loading of a tetraalkoxysilane diluted with the organic solvent, or sometimes water, is preferred because it can form a dense, satisfactory silica film, and an industrially useful continuous process can be constructed.

According to both the first and second aspects of the invention, the silica film grows by deposition onto the metal oxide surface, and therefore a longer film-forming time will result in a thicker silica film. Although the film formation rate will of course fall when the silicic acid in the coating-forming composition has been largely consumed by formation of the coating, successive addition of silicic acid in an amount corresponding to the consumption will allow formation of the silica coating at a continuous practical film formation rate. In particular, by holding the metal oxide particles for a prescribed period of time in the coating-forming composition which contains silicic acid in an amount corresponding to the desired silica film thickness, forming the silica film to consume the silicic acid, removing the silica-coated metal oxide particles out of the system and then adding further silicic acid corresponding to the amount consumed, it is possible to subsequently use the composition for formation of a coating onto a next batch of metal oxide particles, to thus establish an economical, highly productive continuous process.

There are no particular restrictions on the temperature for the coating formation, but it is preferably in the range of 10° C. to 100° C., and more preferably in the range of 20° C. to 50° C. The film formation rate increases with higher temperature, but if the temperature is excessively high, vaporization of the components in the composition may complicate efforts to maintain a constant solution composition. If the temperature is excessively low, the film formation rate is reduced to an impractical level.

The pH during the coating formation may be any alkali pH. However, when forming the silica coating on a metal oxide with a positively pH-dependent solubility, it is preferred to control the pH of the film-forming composition. For production of silica-coated zinc oxide particles, for example, it is preferred to lower the amount of alkali added to control the pH to under 11 during the film formation. If the pH is above 11, the yield of the silica-coated product may be reduced. Furthermore, since a lower alkali content reduces the film-formation rate, it is preferred to raise the film-formation temperature or increase the silicon content to maintain a practical film-formation rate.

After forming the silica coating on the surface of the metal oxide particles, or after forming the silica-coated metal oxide sol if desired, solid/liquid separation can isolate the silica-coated metal oxide particles. The method used may be any common separation method such as filtration, centrifugal sedimentation, centrifugal separation or the like.

The solid/liquid separation may be followed by drying to obtain silica-coated metal oxide particles with a low moisture content. The method used may be any common drying method such as natural drying, warm air drying, vacuum drying, spray drying or the like.

The process for producing silica-coated metal oxide particles used for the invention does not necessarily require firing.

The silica film obtained by the production process described above follows the contour of the complex shape of the metal oxide particles as the substrate, and exhibits satisfactory coating properties and high photocatalytic activity suppressing power even with a thin covering of about 0.5 nm. In addition, since the silica coating can be formed with a very low alkali metal content, the silica film does not dissolve and the properties of the silica-coated metal oxide particles are not altered even in high temperature/high humidity environments.

When a silica-coated metal oxide sol according to the second aspect of the invention is formed, the coating formation may be followed by removal of the unreacted starting materials, alkali and organic solvent and if necessary concentration, to obtain the silica-coated metal oxide sol. The method used may be any common separation method such as evaporation, distillation, membrane separation or the like.

The medium (or solvent) of the silica-coated sol of the invention is not particularly restricted, but is usually selected from among dermatologically innocuous media. For example, water, mineral oil or silicone oil may be used. The medium may be changed from water to another medium by ordinary solvent exchange or membrane separation.

By solid/liquid separation of the silica-coated metal oxide sol followed by drying, it is possible to obtain silica-coated metal oxide particles. The method used for the solid/liquid separation may be any common separation method such as filtration, centrifugal sedimentation, centrifugal separation or the like. The drying method used may be any common drying method such as natural drying, warm air drying, vacuum drying, spray drying or the like. If aggregation of the particles occurs due to the drying, the aggregates may be pulverized. The silica-coated metal oxide sol of the invention has strong covering power on the metal oxide particle bases, and therefore the pulverization will not cause destruction of the silica coating, and will not lower the photocatalytic activity suppressing effect or impair the feel during use. The pulverization method used is not particularly restricted and may employ a jet mill, a high-speed tumbling mill or the like.

Whether using metal oxide particles or using a metal oxide sol, the silica film obtained by the above-mentioned producing process has a ratio I of the absorption peak intensities of the infrared absorption spectrum at 1150–1250 cm$^{-1}$ and 1000–1100 cm$^{-1}$ ($I=I_1/I_2$: where $I_1$ is the maximum absorption peak intensity at 1150–1250 cm$^{-1}$ and $I_2$ is the maximum absorption peak intensity at 1000–1100 cm$^{-1}$) of 0.2 or greater, and refractive index of 1.435 or greater. That is, it is a dense, practical silica coating retaining the original surface properties of the silica film (moistness, smoothness), which has not been hitherto achievable without firing.

The silica film also closely follows the contour of the complex shape of the metal oxide particle base material, and exhibits satisfactory coating properties and high photocatalytic activity suppressing power even with a thin covering of about 0.1 nm. In addition, since the silica coating can be formed with a very low alkali metal content, the silica film does not dissolve and the properties of the silica-coated metal oxide sol is not altered even in high temperature/high humidity environments. The thickness of the silica film is preferably 0.1–100 nm and more preferably 1–20 nm.
(Hydrophobicizing Treatment)

According to the invention, and especially according to the first aspect, the silica-coated metal oxide particles are surface-treated with a hydrophobicizing agent, but if desired, a silica-coated metal oxide sol obtained according to the second aspect may also be surface treated with a hydrophobicizing agent.

The method of surface treatment of the silica-coated metal oxide particles with the hydrophobicizing agent may be any publicly known method so long as it is applicable. Ordinary dry methods, wet methods and spray methods may be used. In the case of a dry method, for example, the method may involve adding a hydrophobicizing agent or an organic solvent solution of a hydrophobicizing agent to metal oxide particles agitated with a mixture such as a V-shaped mixer, Henschel mixer or the like by a method such as spraying, continuing the mixing for uniform attachment to the surface of the powder, drying, and if necessary, heating to achieve firm attachment. In the case of a wet method, the method used may involve dispersion of the metal oxide particles in water or an organic solvent, addition of the hydrophobicizing agent and reaction catalyst, etc., and further mixing followed by filtration and drying. In the case of a spray method, the method may involve spraying of the hydrophobicizing agent or its solution onto the metal oxide particles at high temperature, for coating of the surfaces.

A publicly known method may also be employed for surface treatment of the silica-coated metal oxide sol with the hydrophobicizing agent. According to the invention, a wet method is preferred from the standpoint of not impairing the dispersability and small primary particle size of the starting sol. For example, the wet method may involve addition of the hydrophobicizing agent or its solution and a reaction catalyst, etc. to a dispersion of the metal oxide sol in water, an organic solvent or a mixed solvent, followed by stirring to accomplish surface treatment.

A dry method or spray method may also be used for direct hydrophobicizing of the silica-coated metal oxide particles. Such a method may be any of the publicly known methods mentioned above.
(Hydrophobicizing Agent)

The hydrophobicizing agent used for the invention is not particularly restricted, and for example, there may be used higher fatty acids, higher alcohols and their derivatives, such as waxes, higher fatty acid triglycerides, higher fatty acids, higher fatty acid polyvalent metal salts and higher aliphatic polyvalent metal sulfate salts; organic fluorine-containing compounds such as perfluorinated or partially fluorinated higher fatty acids and higher alcohols; and organic silicon compounds such as silicone oils, organic alkoxysilanes, organic chlorosilanes and silazanes. Higher fatty acid polyvalent metal salts, silicone oils, silane coupling agents and alkoxysilanes are preferably used, and alkoxysilanes and silane coupling agents are particularly preferred from the standpoint of achieving a practical effect.

The silicone oils used for the invention are not particularly restricted, and there may be mentioned dimethylpolysiloxane, methylhydrogenpolysiloxane, methylphenylpolysiloxane and cyclic polydimethylsiloxane. There may also be used alkyl-modified, polyether-modified, amino-modified, mercapto-modified, epoxy-modified and fluorine-modified silicone oils.

There are no particular restrictions on chlorosilanes to be used for the invention, and there may be mentioned trimethylchlorosilane, dimethyldichlorosilane, methyltrichlorosilane, methyldichlorosilane, dimethylvinylchlorosilane, methylvinyldichlorosilane, triphenylchlorosilane, methyldiphenylchlorosilane, diphenyldichlorosilane, methylphenyldichlorosilane and phenyltrichlorosilane.

There are no particular restrictions on silazanes to be used for the invention, and there may be mentioned hexamethyldisilazane, N,N'-bis(trimethylsilyl)urea, N-trimethylsilylacetamide, dimethyltrimethylsilylamine, diethyltrimethylsilylamine and trimethylsilylimidazole.

There are no particular restrictions on organic alkoxysilanes to be used for the invention, and as examples there may be mentioned, silane coupling agents such as vinyltrichlorosilane, vinyltris(β-methoxyethoxy)silane, vinyltrimethoxysilane, vinyltriethoxysilane, γ-(methacryloyloxypropyl)trimethoxysilane, β-(3,4-epoxycyclohexyl)ethyltrimethoxysilane, γ-glycidyloxypropyltrimethoxysilane, γ-glycidoxypropylmethyldiethoxysilane, N-β(aminoethyl)γ-aminopropyltrimethoxysilane, N-β(aminoethyl)γ-aminopropylmethyldiethoxysilane, γ-aminopropyltriethoxysilane, N-phenyl-γ-aminopropyltrimethoxysilane, γ-mercaptopropyltrimethoxysilane and γ-chloropropyltrimethoxysilane, as well as methyltrimethoxysilane, dimethyldimethoxysilane, trimethylmethoxysilane, methyltriethoxysilane, dimethyldiethoxysilane, trimethylethoxysilane, methyldimethoxysilane, methyldiethoxysilane, dimethylethoxysilane, dimethylvinylmethoxysilane, dimethylvinylethoxysilane, phenyltrimethoxysilane, phenyltriethoxysilane, diphenyldimethoxysilane and diphenyldiethoxysilane. There may also be used alkoxysilanes with perfluorinated or partially fluorinated alkyl groups.
(Alkoxysilane Treatment)

Alkylalkoxysilanes represented by the following formula are preferred for use.

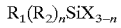 Formula where $R_1$ is an alkyl group of 1–4 carbons or phenyl, $R_2$ is a hydrogen atom, alkyl group of 1–4 carbons or phenyl, X is an alkoxyl group of 1–4 carbons and n is an integer of 0–2.

According to the invention, the surface treatment with the alkoxysilane may be by either a liquid phase method or dry method, but a liquid phase method is preferred from the following viewpoint. Specifically, after contacting the metal oxide particles with the silica coating-forming composition to form the silica coating, the hydrophobicizing agent may be added without separating the powder, or if necessary, the alkali, water and solvent may be added and the silica-coated metal oxide surface treatment carried out continuously with the hydrophobicizing agent. This method is an industrially advantageous method which allows the intermediate separation and purification steps to be omitted.

A liquid phase is particularly preferred especially according to the second aspect of the invention, when an alkylalkoxysilane is used as the hydrophobicizing agent for surface treatment. Specifically, after silica coating of the metal oxide particles in the sol by the method described above, the hydrophobicizing agent may be added without separating the silica-coated metal oxide particles, or if necessary, the water, organic solvent and alkali may be added to form a composition with a water/organic solvent ratio in the range of 0.1–10 and a silicon content derived from the alkylalkoxysilane of 0.0001–5 moles/liter, for selective deposition of the alkylalkoxysilane reaction product on the surfaces of the silica-coated metal oxide particles. This method involves no drying step, and is therefore an industrially advantageous method which allows the intermediate solid separation step to be omitted, without impairing the dispersability and small primary particle size of the starting sol.

The hydrophobicizing composition in the process for production of a surface-hydrophobicized silica-coated metal sol using an alkylalkoxysilane has a water/organic solvent volume ratio in the range of 0.1–10 and an alkylalkoxysilane-derived silicon content in the range of 0.0001–5 moles/liter. The silicon content, water, water/organic solvent ratio, alkali, organic solvent, temperature, pH and separation/purification step for this composition may be the same as described for the silica coating-forming composition. Furthermore, although this composition is obtained by adding an alkylalkoxysilane instead of a silicic acid-producing precursor to the above-mentioned silica coating-forming composition after the silica coating has been formed, the composition and conditions need not necessarily be identical. For example, the reaction rate of the alkylalkoxysilane differs from the silicic acid-producing precursor, an alkali, water or solvent may be added if necessary, and the water/organic solvent ratio, silicon content, pH, temperature and other reaction conditions may be selected to result in a practical reaction rate within the aforementioned restricted ranges.

(Coverage for Hydrophobicizing Agent Treatment)

The coverage of the hydrophobicizing agent is sufficient so long as it is the minimum coverage allowing the hydrophobicizing agent to completely coat the surfaces of the silica-coated metal oxide particles of the starting material The coverage may be calculated by the following formula:

$$\frac{\text{Metal oxide particle mass (g)} \times \text{Specific surface area } (m^2/g)}{\text{Minimum coating area of hydrophobicizing agent } (m^2/g)}$$

The upper limit for the amount of hydrophobicizing agent added cannot be specified for all cases, but an excess is not economical as it will result in deposition elsewhere than on the surfaces of the metal oxide particles. For ordinary silica-coated metal oxide particles, it is preferably no more than 30 wt % and more preferably no more than 20 wt %.

(Properties of Silica-coated Metal Oxide Particles and Sol)

The silica film thickness of the silica-coated metal oxide particles and the surface-hydrophobicized silica-coated metal oxide particles (including silica-coated metal oxide sol, same hereunder) is 0.1–100 nm, and preferably 0.5–25 nm. At below this range, it may not be possible to obtain a cosmetic material with an adequate suppressing effect on photocatalytic activity, while an amount above this range may not give a cosmetic material with an adequate ultraviolet-screening function, and is uneconomical.

The photocatalytic activity of the silica-coated metal oxide particles and surface-hydrophobicized silica-coated metal oxide particles, as measured by the tetralin autooxidation method, is 60 Pa/min or lower. At above this range, it may not be possible to achieve an adequate photocatalytic activity-suppressing effect.

The surface-hydrophobicized silica-coated metal oxide particles used for the invention have a primary particle size of 5–500 nm and preferably 5–120 nm, and a secondary particle size of 0.5–10 μm. The silica-coated metal oxide particles of the silica-coated metal oxide sol of the invention have a primary particle size of 1–100 nm and preferably 5–20 nm. Outside of these ranges, it may not be possible to obtain a cosmetic material with a satisfactory feel during use and high ultraviolet-screening function. Primary particles and secondary particles are defined in the invention according to Kubo, K. et al., "Funtai (Particles)", pp.56–66, 1979.

The powder dynamic friction coefficient of the silica-coated metal oxide particles and surface-hydrophobicized silica-coated metal oxide particles used for the invention, as measured by the glass plate method, is preferably no more than 0.54, and more preferably no more than 0.49. If it exceeds 0.54, it may not be possible to obtain a cosmetic material with a satisfactory feel during use.

The pigment decoloration rate of the silica-coated metal oxide particles and surface-hydrophobicized silica-coated metal oxide particles used for the intention, as measured by the Sunset Yellow method, is preferably no more than 0.06 and, even more preferably no more than 0.02. If it exceeds 0.06, the photocatalytic activity-suppressing effect may be insufficient, and it may not be possible to obtain a cosmetic material with high storage stability.

The decomposition rate of the organic-based ultraviolet absorber by the silica-coated metal oxide particles and surface-hydrophobicized silica-coated metal oxide particles used for the invention, as measured by the parasol method, is preferably no more than 0.02, and more preferably no more than 0.01. If it is less than 0.02, the photocatalytic activity-suppressing effect may be insufficient, and it may not be possible to obtain a cosmetic material with low decomposition of the organic-based ultraviolet absorber.

When surface-hydrophobicized silica-coated metal oxide particles according to the invention are used, the high visible light transmittance with high ultraviolet-screening function gives a highly transparent cosmetic.

Silica-coated metal oxide particles used for the invention need no particular firing. They may, of course, be used with firing, however.

The silica-coated metal oxide particles and surface-hydrophobicized silica-coated metal oxide particles obtained from a silica-coated metal oxide sol of the invention have a small primary particle size, low aggregation and satisfactory dispersability, and therefore exhibit a high ultraviolet-screening function and high visible light transmittance. Furthermore, since they are covered with a dense, practical silica coating, they exhibit a high photocatalytic activity-suppressing effect, low degeneration of other added cosmetic components, and satisfactory feel during use and smoothness. Thus, by combining silica-coated metal oxide particles and surface-hydrophobicized silica-coated metal oxide particles obtained from a silica-coated metal oxide sol and surface-hydrophobicized silica-coated metal oxide sol or silica-coated metal oxide sol and surface-hydrophobicized silica-coated metal oxide sol, it is possible to obtain an ultraviolet-screening cosmetic material with satisfactory storage stability, safety and excellent transparency and feel during use. A surface-hydrophobicized silica-coated metal oxide sol and surface-hydrophobicized silica-coated metal oxide particles are preferably used in an oil-based cosmetic material, W/O emulsion cosmetic material or water-repellent cosmetic material resistant to cosmetic disintegration by perspiration and moisture.

The cosmetic material obtained from a silica-coated metal oxide sol, according to the invention, comprises the aforementioned silica-coated metal oxide particles and surface-hydrophobicized silica-coated metal oxide particles obtained from a silica-coated metal oxide sol and/or surface-hydrophobicized silica-coated metal oxide sol or silica-coated metal oxide sol and surface-hydrophobicized silica-coated metal oxide sol, and it may be produced by a common process using common starting materials that are compatible with cosmetic materials.

(Cosmetic Material)

The cosmetic material of the invention may be produced by a common production process using common starting materials which are compatible with cosmetic materials comprising silica-coated metal oxide particles and surface-hydrophobicized silica-coated metal oxide particles. (This meaning includes silica-coated metal oxide sols, same hereunder.)

The cosmetic material of the invention is not particularly restricted so long as it comprises powder and an oil-based portion, and the powder may also be dispersed in a solvent or solution. As examples there may be mentioned, farina, foundation, powder, cheek rouge, eye shadow, lipstick, eyeliner, mascara, eyebrow makeup, cream, essence, lotion, cosmetic water, emulsion, mousse and the like. Particularly preferred are oil-based cosmetic materials, W/O emulsion cosmetic materials and water-repellent cosmetic materials resistant to cosmetic disintegration by perspiration and moisture.

Powder components and oil components compose the cosmetic material of the invention. Powder components include, in addition to silica-coated metal oxide powders and surface-hydrophobicized silica-coated metal oxide powders, also constitutional pigments (for example, mica, talc, kaolin, calcium carbonate, magnesium carbonate, silicic anhydride, aluminum oxide, barium sulfate, etc.), white pigments (for example, titanium dioxide, zinc oxide, etc.) and colored pigments (for example, iron oxide red, iron oxide yellow, iron oxide black, chromium oxide, ultramarine, iron blue, carbon black, etc.), and these may be appropriately combined. In addition, spherical powders (for example, nylon powder, polymethyl methacrylate powder, etc.) may be used for an enhanced feel during use.

As oil components to be included in the cosmetic material of the invention there may be mentioned liquid paraffin, squalane, castor oil, glyceryl diisostearate, glyceryl triisostearate, glyceryl tri-2-ethylhexanoate, isopropyl myristate, glyceryl triisostearate, dimethylpolysiloxane, methylphenylpolysiloxane, vaseline, diisostearyl malate and purified lanolin.

The amount of oil component combined with the solid powder cosmetic material is preferably 3 wt % or more and more preferably 10–90 wt %.

The oil component may also include an organic-based ultraviolet absorber. An organic-based ultraviolet absorber is an organic compound with a function of protecting the skin by absorbing ultraviolet rays and converting them to energy such as heat, vibration, fluorescence, radicals or the like. AS ultraviolet absorbers that may be used in the cosmetic material of the invention there may be mentioned, with no particular restrictions, benzophenone-based, salicylic acid based, PABA-based, cinnamic acid-based, dibenzoylmethane-based and urocanic acid-based ultraviolet absorbers. The addition amount is in the range of 0.1–10 wt %, but the amount is preferably determined as appropriate depending on the ultraviolet absorbing capacity of the absorber. The silica-coated metal oxide particles used for the invention have a high photocatalytic activity-suppressing effect, and therefore even when used in combination with organic-based ultraviolet absorbers, decomposition of the absorber is inhibited and a cosmetic material with a high ultraviolet-screening function can be obtained.

Existing emulsifiers may also be added in ordinary amounts to the cosmetic material of the invention. For example, there may be used any of the emulsions described in "Cosmetic Material standards, 2nd Edition, Annotated" edited by Nihon Koteisho Kyokai, 1984 (Yakuji Nippo Publishing), "Cosmetic Material Standards: Standardized Mixing Components", edited by Ministry of Health and welfare, Pharmaceutical Affairs Dept., 1993 (Yakuji Nippo Publishing), "Supplementary Cosmetic Material Standards: Standardized Mixing Components", edited by Ministry of Health and welfare, Pharmaceutical Affairs Dept., 1993 (Yakuji Nippo Publishing), "Cosmetic Classification and Approval Standards", edited by Ministry of Health and Welfare, Pharmaceutical Affairs Dept., 1993 (Yakuji Nippo Publishing) and "Encyclopedia of Cosmetic Material Terms", 1991, Nikko chemicals. Tocopherylphosphate esters may also be used as emulsifiers.

The cosmetic material of the invention used in combination with or mixed with known anti-inflammatory components or antiphlogistic components to aid in preventing inflammation by ultraviolet rays. There are no particular restrictions on antiphlogistic components that may be added to the cosmetic material of the invention, and there may be mentioned aniline derivative-based antiphlogistics, salicylic acid derivative-based antiphlogistics, pyrazolone derivative-based antiphlogistics, indomethacine-based antiphlogistics, mefenamic acid-based antiphlogistics, antipodagrics, antispasmodics, expectorants, bronchodilators, respiratory enhancers, antihistamines, anti-allergic agents and anti-inflammatory enzyme agents When an antioxidant, as a substance with an antioxidizing effect, is combined with a cosmetic material comprising silica-coated metal oxide particles and surface-hydrophobicized silica-coated metal oxide particles according to the invention, it is possible to further minimize the photocatalytic activity of the silica-coated metal oxide particles by inhibiting generation of free radicals by ultraviolet rays, thereby giving a cosmetic material with very low phototoxicity. As antioxidants that may be used for an effect of minimizing photocatalytic activity in cosmetic materials according to the invention there may be mentioned, with no particular restrictions, vitamin A, β-carotene, astaxanthin, vitamin B, vitamin C, magnesium L-ascorbate-2-phosphate, sodium L-ascorbate-2-phosphate, sodium magnesium L-ascorbate-2-phosphate, L-ascorbate-2-glycoside, L-ascorbate-2-phosphate-5,6-benzylidene, natural vitamin E, dl-α-tocopherol, dl-α-tocopherylacetate ester, sodium dl-α-tocopherylphosphate, ubiquinones and their vitamin derivatives, cysteine, glutathione, glutathione peroxidase, SOD, catalase, citric acid, phosphoric acid, polyphenols, catechins, tea extract, kojic acid, nucleic acid, hydroquinone and albutin. Any one or combination of two or more of these antioxidants may be selected from among this group.

A cosmetic material according to the invention may also contain other components commonly added to cosmetic and other compositions, such as oils and fats, waxes, hydrocarbons, fatty acids, alcohols, polyhydric alcohols, sugars, esters, metal soaps, water-soluble polymer compounds, surfactants, antioxidants, antimicrobial and antiseptic agents, vitamins, hormones, coloring agents and the like.

The amount of the silica-coated metal oxide particles and surface-hydrophobicized silica-coated metal oxide particles in a cosmetic material of the invention is preferably in the range of 1–50 wt % and more preferably 5–30 wt % with respect to the cosmetic material.

Generally speaking, for silica-coated titania particles it is preferred to use titania with a high proportion of a low photocatalytic rutile type rather than an anatase type.

However, silica-coated titania particles and surface-hydrophobicized silica-coated titania particles used in a cosmetic material according to the invention can minimize generation of free radicals by ultraviolet rays, and therefore give a cosmetic material with low phototoxicity regardless of the crystal type.

A cosmetic material comprising the silica-coated metal oxide particles and surface-hydrophobicized silica-coated metal oxide particles according to the invention not only has a high ultraviolet-screening function, but also has an excellent feel during use with no squeaky feel or undesirablly low extension even when the metal oxide particles are present at high concentration. The cosmetic material of the invention has high transparency, and exhibits no paleness in the cosmetic finish as when conventional titania particles are used. Furthermore, since photocatalytic activity by the metal oxide is adequately suppressed, degeneration of the other added components in the composition is not promoted, and excellent storage stability results organic-based ultraviolet absorbers may also be included, to achieve a higher ultraviolet-screening function. In addition, by adding anti-oxidants with antioxidizing effects, it is possible to greatly reduce generation of active oxygen and the like, and thus increase the safety for human use.

The film thickness and refractive index of the silica film of the invention may be measured for a silica film formed on a silicon wafer accumulated in the system during synthesis of the silica-coated metal oxide particles. The silicon wafer has the same silica coating as that formed on the metal oxide particles. The refractive index of the silica film may be measured with an ellipsometer (LASSER ELLIPSOMETER ESM-1A, by ULVAC). The film thickness may be measured using a level-measuring instrument. The transmission infrared absorption spectrum of the surface-hydrophobicized silica-coated metal oxide particles (FT-IR-8000 by JASCO Corp.) may be measured using the KBr method.

The primary particle size and silica film thickness of the silica-coated metal oxide particles and surface-hydrophobicized silica-coated metal oxide particles may be determined from a transmission electron microscope image. The secondary particle size may be measured by the laser light scattering method (MICROTRACK MK-II, Nikkiso Corp.). The total alkali metal content may be measured by flame analysis after dissolving the silica-coated metal oxide particles/surface-hydrophobicized silica-coated metal oxide particles in sulfuric acid.

The photocatalytic activity, or initial oxygen consumption rate, of the silica-coated metal oxide particles and surface-hydrophobicized silica-coated metal oxide particles may be measured by the tetralin autooxidation method (Seino, M., "Titanium Oxide—Properties and Application Techniques", Gihodo Publishing, pp.196–197, 1991). The measuring conditions are a temperature of 40° C., 20 ml tetralin and 0.02 g of metal oxide particles.

The light transmittance, organic-based ultraviolet absorber decomposition rate, powder dynamic friction coefficient, pigment decoloration rate and water repellency of the silica-coated metal oxide particles and surface-hydrophobicized silica-coated metal oxide particles of the invention may be measured by the COSMAL method, parasol method, glass plate method, Sunset Yellow method and methanol solution method, as described in the present specification.

EXAMPLES

Examples of the present invention will now be explained in detail, with the understanding that the invention is in no way limited to these examples.

Production Example 1a

Production of Silica-coated Titania Particles

Suspension 1 was prepared by mixing 7.07 kg of deionized water, 25.43 kg of ethanol (Junsei Chemical Co., Ltd.) and 1.143 kg of 25 wt % ammonia water (Taisei Kako Co.) in a 30 L reactor and then dispersing therein 1.765 kg of titania particles (Titania F-4 by Showa Titanium Co., primary particle size: 30 nm). Next, 1.53 kg of tetraethoxysilane (Nacalai Tesque, Inc.) and 659 g of ethanol were combined to prepare Solution 1. After adding Solution 1 at a fixed rate over a period of 9 hours to Suspension 1 while stirring with a stirring blade, the mixture was allowed to mature or age for 12 hours. The silica coating formation and maturation or aging were carried out at 25° C.

The solid portion was then filtered out by centrifugal filtration and vacuum dried at 50° C. for 12 hours to obtain silica-coated titania particles.

Production Example 1b

Production of Surface-hydrophobicized Silica-coated Titania Particles

The same procedure was carried out up to silica film formation and maturation in the same manner as Production Example 1a. Suspension 2 was prepared by adding 430 g of 25 wt % ammonia water with the silica-coated titania particles still present in the reaction solution, and stirring. Next, 330 g of dimethyldiethoxysilane (TSL8122, Toshiba Silicon) and 330 g of ethanol were added thereto to prepare Solution 2. After adding Solution 2 at a fixed rate over a period of 9 hours to Suspension 2 while stirring, the mixture was allowed to mature for 12 hours. The surface coating and maturation were carried out at 45° C.

The solid portion was then filtered out by centrifugal filtration and vacuum dried at 50° C. for 12 hours to obtain surface-hydrophobicized silica-coated titania particles.

Production Example 2a

Production of Silica-coated Zinc Oxide Particles

Suspension 3 was prepared by mixing 20.19 kg of deionized water, 19.8 kg of ethanol (Junsei Chemical Co., Ltd.) and 204 mL of 25 wt % ammonia water (Taisei Kako Co.) in a 50 L reactor and then dispersing therein 1.914 kg of zinc oxide particles (MZ0350 by Sumitomo Osaka Cement, primary particle size: 37 nm). Next, 740 kg of tetraethoxysilane (Nacalai Tesque, Inc.) and 488 g of ethanol were added thereto to prepare Solution 3.

After adding Solution 3 at a fixed rate over a period of 9 hours to Suspension 3 while stirring with a stirring blade, the mixture was allowed to mature for 12 hours. The silica coating formation and maturation were carried out at 45° C. The solid portion was then filtered out by centrifugal filtration and vacuum dried at 50° C. for 12 hours to obtain silica-coated zinc oxide particles.

Production Example 2b

Production of Surface-hydrophobicized Silica-coated Zinc Oxide Particles

The same procedure was carried out up to silica film formation and maturation in the same manner as Production Example 2a. Suspension 4 was prepared by adding 136 mL of 25 wt % ammonia water and 200 mL of deionized water with the silica-coated zinc oxide particles still present in the reaction solution, and stirring. Next, 400 g of dimethyldiethoxysilane (8122, Toshiba Silicon) and 400 g of ethanol were added thereto to prepare Solution 4. After adding Solution 4 at a fixed rate over a period of 12 hours to Suspension 4 while stirring with a stirring blade, the mixture was allowed to mature for 12 hours. The surface coating and maturation were carried out at 45° C.

The solid portion was then filtered out by centrifugal filtration and vacuum dried at 50° C. for 12 hours to obtain surface-hydrophobicized silica-coated zinc oxide particles.

Production Examples 3a–5a

Production of Silica-coated Metal Oxide Particles

Cerium oxide particles, zirconium oxide particles and iron oxide red particles were used instead of the titania in Production Example 1, under the same production conditions, to obtain silica-coated cerium oxide particles, silica-coated zirconium oxide particles and silica-coated iron oxide red particles.

Production Examples 3b–5b

Production of Surface-hydrophobicized Silica-coated Metal Oxide Particles

Cerium oxide particles, zirconium oxide particles and iron oxide red particles were used instead of the titania in Production Example 1b, under the same production conditions, to obtain silica-coated cerium oxide particles, silica-coated zirconium oxide particles and silica-coated iron oxide red particles.

Upon measuring the transmission infrared absorption spectra for the silica-coated metal oxide particles obtained in Production Examples 1a–5a by the KBr method, absorption attributed to Si—O—Si stretching vibration was observed at 1000–1200 $cm^{-1}$ in all cases, whereas no absorption was observed from C—H stretch vibration at 2800–3000 $cm^{-1}$, and thus the coating produced was identified as silica.

The primary particle size, secondary particle size, silica film thickness, infrared absorption spectrum peak intensity ratio I, silica film refractive index, photocatalytic activity by the tetralin autooxidation method, water repellency and total alkali metal concentration were also measured.

The primary particle size, secondary particle size, silica film thickness, photocatalytic activity by the tetralin autooxidation method and water repellency were also measured for the surface-hydrophobicized silica-coated titania particles of Production Examples 1b–5b. The results are shown in Table 1.

TABLE 1

Properties of metal oxide particles (1)

| Metal oxide particles | Primary particle size nm | Secondary particle size μm | Film thickness nm | I value | Refractive index | Photocatalytic activity mmH$_2$O/min | Water repellency |
|---|---|---|---|---|---|---|---|
| Prod. Ex. 1a | 30 | 2.6 | 2 | 0.5 | 1.447 | 4.9 | − |
| Prod. Ex. 2a | 37 | 3.5 | 4 | 0.5 | 1.445 | 4.1 | − |
| Prod. Ex. 3a | 95 | 8.3 | 12 | 0.4 | 1.450 | 3.8 | − |
| Prod. Ex. 4a | 80 | 4.0 | 10 | 0.4 | 1.444 | 3.4 | − |
| Prod. Ex. 5a | 90 | 9.1 | 11 | 0.4 | 1.442 | 3.2 | − |
| Prod. Ex. 1b | 30 | 1.8 | 2 | | | 4.9 | + |
| Prod. Ex. 2b | 37 | 2.4 | 4 | | | 4.0 | + |
| Prod. Ex. 3b | 95 | 3.6 | 12 | | | 3.8 | + |
| Prod. Ex. 4b | 80 | 2.9 | 10 | | | 3.4 | + |
| Prod. Ex. 5b | 90 | 4.6 | 11 | | | 3.2 | + |

+: Water repellency, no particle sedimentation
−: No water repellency, particle sedimentation in solution, solution turbidity

Production Example 6

Production of Silica-coated Titania Sol

Suspension 1 was prepared by mixing 25.10 kg of ethanol (junsei Chemical Co., Ltd.) and 1.14 kg of 25 wt % ammonia water (Taisei Kako Co.) in a 50 L reactor and then dispersing therein 8.83 kg of an aqueous titania sol (titania concentration: 20.0 wt %, primary particle size: 16 nm, surface area: 136 g/$m^2$). Next, 2.30 kg of tetraethoxysilane (Nacalai Tesque, Inc.) and 990 g of ethanol were added thereto to prepare Solution 2. After adding Solution 2 at a fixed rate over a period of 9 hours to Suspension 1 while stirring with a stirring blade, the mixture was allowed to mature for 12 hours. The silica coating formation and maturation were carried out at 25° C. The ammonia and ethanol were then distilled off to obtain a silica-coated titania sol.

Production Example 7

Production of Silica-coated Zinc Oxide Sol

Suspension 1 was prepared by mixing 2.96 kg of deionized water, 19.00 kg of ethanol (Junsei Chemical Co., Ltd.) and 210 mL of 25 wt % ammonia water (Taisei Kako Co.) in a 50 L reactor and then dispersing therein 19.14 kg of an aqueous zinc oxide sol (zinc oxide concentration: 10.0 wt %, primary particle size: 19 nm, surface area: 122 g/$m^2$). Next, 1.92 kg of tetraethoxysilane (Nacalai Tesque, Inc.) and 1.28 kg of ethanol were added thereto to prepare Solution 2. After adding Solution 2 at a fixed rate over a period of 9 hours to Suspension 1 while stirring with a stirring blade, the mixture was allowed to mature for 12 hours. The silica coating formation and maturation were carried out at 45° C. The ammonia and ethanol were then distilled off to obtain a silica-coated zinc oxide sol.

Production Examples 8–10

Production of Silica-coated Metal Oxide Sol

Cerium oxide sol, zirconium oxide sol and iron oxide red sol were used instead of the titania sol in Production Example 6, under the same production conditions, to obtain silica-coated cerium oxide sol, silica-coated zirconium oxide sol and silica-coated iron oxide red sol.

The average primary particle size, silica film thickness, infrared absorption spectrum peak intensity ratio (I value), silica film refractive index and BET surface area were also measured. The results are summarized in Table 2.

Production Example 11

Production of Surface-hydrophobicized Silica-coated Titania Sol

After carrying out the same procedure up to silica film formation and maturation in the same manner as Production Example 6, Suspension 1 was prepared by adding 880 g of 25 wt % ammonia water without separating the silica-coated titania sol, and stirring. Next, 680 g of dimethyldiethoxysilane (TSL8122, Toshiba Silicon) and 680 g of ethanol were added thereto to prepare Solution 2. The amount of dimethyldiethoxysilane added was 1.5 times the minimum coverage as calculated by the formula given above. After adding Solution 2 at a fixed rate over a period of 9 hours to Suspension 1 while stirring, the mixture was allowed to mature for 12 hours. The surface coating and maturation were carried out at 65° C. The ammonia and ethanol were then distilled off to obtain a surface-hydrophobicized silica-coated titania sol.

Production Example 12

Production of Surface-hydrophobicized Silica-coated Zinc Oxide Sol

After carrying out the same procedure up to silica film formation and maturation in the same manner as Production Example 7, Suspension 1 was prepared by adding 330 g of deionized water and 225 g of 25 wt % ammonia water without separating the silica-coated zinc oxide sol still present in the reaction solution, and stirring. Next, 660 g of dimethyldiethoxysilane (TSL8122, Toshiba Silicon) and 660 g of ethanol were added thereto to prepare Solution 2. The amount of dimethyldiethoxysilane added was 1.5 times the minimum coverage as calculated by the formula given above. After adding Solution 2 at a fixed rate over a period of 9 hours to Suspension 1 while stirring, the mixture was allowed to mature for 12 hours. The surface coating and maturation were carried out at 45° C. The ammonia and ethanol were then removed by distillation to obtain a surface-hydrophobicized silica-coated zinc oxide sol.

Production Examples 13–15

Production of Surface-hydrophobicized Silica-coated Metal Oxide Sols

After carrying out the same procedure up to silica film formation and maturation in the same manner as Production Examples 8 to 10, Suspension 1 was prepared by adding 650 g of 25 wt % ammonia water with the silica-coated metal oxide sol still present in the reaction solution, and stirring. Next, Solution 2 was prepared by mixing dimethyldiethoxysilane (TSL8122, Toshiba Silicon) in an amount of 1.5 times the minimum coverage and an equivalent amount of ethanol. After adding Solution 2 at a fixed rate over a period of 9 hours to Suspension 1 while stirring, the mixture was allowed to mature for 12 hours. The surface coating and maturation were carried out at 45° C. The ammonia and ethanol were then removed by distillation to obtain a surface-hydrophobicized silica-coated cerium oxide sol, surface-hydrophobicized silica-coated zirconium oxide sol and surface-hydrophobicized silica-coated iron oxide red sol.

The water repellency of the surface-hydrophobicized silica-coated metal oxide sols obtained in Production Examples 11 to 15 were measured by the methanol method. Specifically, 10 g of 20% aqueous methanol was placed in a test tube, the test substance was added to 1 wt % and vigorously stirred, after which the mixture was allowed to stand and the water repellency was judged after one hour. All the sols exhibited satisfactory water repellency. The primary particle sizes, silica film thicknesses and BET surface area were then measured. The results are summarized in Table 2.

TABLE 2

| | Properties of metal oxide sols (1) | | | | |
|---|---|---|---|---|---|
| Example | Primary particle size nm | Surface area $m^2/g$ | Silica film thickness nm | I value | Refractive index |
| Prod. Ex. 6 | 16 | 136 | 1 | 0.5 | 1.452 |
| Prod. Ex. 7 | 19 | 122 | 1 | 0.5 | 1.453 |
| Prod. Ex. 8 | 20 | 116 | 1.4 | 0.5 | 1.446 |
| Prod. Ex. 9 | 22 | 110 | 1.5 | 0.4 | 1.450 |
| Prod. Ex. 10 | 27 | 80 | 2 | 0.4 | 1.445 |
| Prod. Ex. 11 | 17 | 130 | 1 | | |
| Prod. Ex. 12 | 20 | 119 | 1 | | |
| Prod. Ex. 13 | 20 | 111 | 1.4 | | |
| Prod. Ex. 14 | 22 | 104 | 1.5 | | |
| Prod. Ex. 15 | 27 | 78 | 2 | | |

Production Examples 16–25

Production of Metal Oxide Particles Derived from Silica-coated Metal Oxide Sols and Surface-hydrophobicized Silica-coated Metal Oxide Sols The solid portions of the silica-coated metal oxide sols obtained in Production Examples 6–10 and the surface-hydrophobicized silica coated metal oxide sols obtained in Production Examples 11–15 were separated by centrifugal filtration, vacuum dried at 50° C. for 12 hours, and then pulverized with a jet mill to obtain metal oxide particles derived from silica-coated metal oxide sols and surface-hydrophobicized silica-coated metal oxide sols.

(Water Repellency Measurement: Methanol Method)

The five types of surface-hydrophobicized silica-coated metal oxide particles obtained in Production Examples 1b–5b and the five types of silica-coated metal oxide particles obtained in Production Examples 1a–5a were used as test substances for measurement of the water repellency by the methanol method.

Specifically, 10 g of 20% aqueous methanol was placed in a test tube, the test substance was added to 1 wt % and vigorously stirred, and then allowed to stand. After one hour, the water repellency was evaluated according to the following measuring standard. The results are shown in Table 1.

The surface-hydrophobicized silica-coated metal oxide particles of the invention exhibited satisfactory water repellency. In contrast, the silica-coated metal oxide particles of the prior art did not exhibit water repellency.

(Light Transmittance Measurement: COSMAL Method)

Surface-hydrophobicized silica-coated titania particles (Production Example 1b), surface-hydrophobicized silica-coated zinc oxide particles (Production Example 2b), silica-coated titania particles (Production Example 1a), silica-coated zinc oxide particles (Production Example 2a) and two types of conventionally surface-hydrophobicized titania particles (MT100T by Teika Co. and TTO-55A by Ishihara Sangyo) were used as test substances for measurement of the light transmittance by the COSMAL method.

The two types of silica-coated metal oxide sols obtained in Production Examples 6 and 7 and the two types of surface-hydrophobicized silica-coated metal oxide sols obtained in Production Examples 11 and 12 were used as test substances for measurement of the light transmittance by the COSMAL method.

Specifically, the test substance was dispersed in polyglyceryl triisostearate (COSMAL 43) to prepare a 1% concentration slurry, and the slurry was placed in a quartz glass cell with a thickness of 0.1 mm for measurement of the light transmittance with a spectrophotometer (SHIMADZU UV-160). The absorbances at a wavelength of 360 nm (A360), the absorbances at a wavelength of 530 nm (A530) and the ratio of both (A360/A530) are shown in Tables 3 and 4.

The surface-hydrophobicized silica-coated metal oxide particles and silica-coated metal oxide sols of the invention had improved solution dispersion properties, and therefore exhibited higher screening functions in the ultraviolet region (A360) and higher transmittance in the visible light region (1/A530), as compared to the conventional silica-coated metal oxide particles. Consequently, cosmetic materials of the invention comprising these surface-hydrophobicized silica-coated titania particles and silica-coated metal oxide sols are expected to offer higher ultraviolet screening function and visible light transparency (A360/A530).

TABLE 3

Light transmittance of metal oxide particles

| Metal oxide particles | A360 | A530 | A360/A530 |
| --- | --- | --- | --- |
| Prod. Ex. 1a | 1.390 | 0.708 | 1.96 |
| Prod. Ex. 1b | 1.422 | 0.562 | 2.53 |
| Prod. Ex. 2a | 0.930 | 0.202 | 4.60 |
| Prod. Ex. 2b | 0.932 | 0.185 | 5.03 |

TABLE 4

Light transmittance of metal oxide sols

| Metal oxide sol | A360 | A530 | A360/A530 |
| --- | --- | --- | --- |
| Prod. Ex. 6 | 1.543 | 0.504 | 3.1 |
| Prod. Ex. 11 | 1.572 | 0.481 | 3.3 |
| Prod. Ex. 7 | 0.987 | 0.162 | 6.1 |
| Prod. Ex. 12 | 1.019 | 0.160 | 6.4 |

(Measurement of Hydroxy Radical Generation)

An antioxidant mixture (mixture of 5% β-carotene, 5% astaxanthin, 20% magnesium L-ascorbate-2-phosphate, 10% sodium L-ascorbate-2-phosphate, 10% L-ascorbate-2-glucoside, 10% L-ascorbate-2-phosphate-5,6-benzylidene, 10% natural vitamin E, 5% dl-α-tocopherol, 5% dl-α-tocopheryl acetic acid ester, 5% sodium dl-α-tocopherylphosphate, 5% citric acid, 5% phosphoric acid and 5% epigallocatechin: proportions in percent by weight) was prepared.

A combination of this antioxidant mixture with the silica-coated titania particles of Production Example 1 in a weight ratio of 1:1, the silica-coated titania particles of Production Example 1 alone and uncoated titania powder alone were each used to prepare aqueous suspensions with the same titania concentration (0.5%), and the hydroxy radical generation under light irradiation was measured by electron spin resonance measurement using DMPO as the radical trapping agent.

The hydroxy radical generation was lowest when antioxidants were combined with the silica-coated titania particles, next lowest with the silica-coated titania particles alone, and highest with the uncoated titania particles.

(Measurement of Photocatalytic Activity: Tetralin Autooxidation Method)

The five types of silica-coated metal oxide sols obtained in Production Examples 6–10 and the five types of surface-hydrophobicized silica-coated metal oxide sols obtained in Production Examples 11–15 were used as test substances for measurement of the photocatalytic activity by the tetralin autooxidation method. The results are summarized in Table 6. All of the silica-coated metal oxide sols and surface-hydrophobicized silica-coated metal oxide sols had values of 60 Pa/min or lower, thus exhibiting photocatalytic activity suppression equivalent to that of conventional silica-coated metal oxide powder.

(Organic-based Ultraviolet Absorber Decomposition Rate Measurement: Parasol Method)

Five types of surface-hydrophobicized silica-coated metal oxide particles obtained in Production Examples 1b–5b and five types of uncoated metal oxide particles corresponding to each of the five types of silica-coated metal oxide particles obtained in Production Examples 1a–5a, and two types of conventionally surface-treated titania particles (MT100T by Teika Co. and TTO-55A by Ishihara Sangyo) were used as test substances for measurement of the organic-based ultraviolet absorber decomposition rate measurement by the parasol method.

Also, the five types of silica-coated metal oxide sols obtained in Production Examples 6–10 and the five types of surface-hydrophobicized silica-coated metal oxide sols obtained in Production Examples 11–15 were used as test substances for measurement of the organic-based ultraviolet absorber decomposition rate measurement by the parasol method.

Specifically, each test substance was dispersed in a polyethylene glycol 300 solution containing 4-tert-butyl-4'-methoxydibenzoylmethane (Parasol 1789) (0.045 wt % concentration of Parasol 1789), to prepare slurries each at 1 wt %. A 1.5 g portion of each slurry was placed in a glass vessel, and after ultraviolet irradiation (1.65 mW/cm$^2$), 1 g was sampled and 2 mL of isopropyl alcohol, 2 mL of hexane and 3 mL of distilled water were added in that order. The mixture was stirred, the Parasol 1789 was extracted into the hexane phase, and the absorbance (340 nm) of the hexane phase with an optical path of 1 mm was periodically measured with a spectrophotometer (SHIMADZU UV-160) (ultraviolet irradiation at 3 time points after 0, 5 and 10 hours). The reduction rate in the absorbance at 340 nm (ΔA340/h) was determined. The results are shown in Tables 5 and All of the surface-hydrophobicized silica-coated metal oxide particles and silica-coated metal oxide sole according to the invention had values of 0.01(ΔA340/h) or lower, thus exhibiting decomposition properties equivalent to that of conventional silica-coated metal oxide particles. Consequently, cosmetic materials comprising these surface-hydrophobicized silica-coated metal oxide particles and silica-coated metal oxide sols can clearly be used in combination with organic-based ultraviolet screening substances. It may be concluded that even with surface treatment by hydrophobicizing agents, there is no impairment of the low decomposition properties of the ultraviolet absorbers in conventional silica-coated surface-treated metal oxide particles.

(Powder Dynamic Friction Coefficient Measurement: Glass Plate Method)

Five types of surface-hydrophobicized silica-coated metal oxide particles obtained in Production Examples 1b–5b and five types of uncoated metal oxide particles corresponding to each of the five types of silica-coated metal oxide particles obtained in Production Examples 1a–5a, and two types of conventionally surface-treated titania particles (MT1000T by Teika Co. and TTO-55A by Ishihara Sangyo) were used as test substances for measurement of the powder dynamic friction coefficient by the glass plate method.

Also, metal oxide particles derived from the five types of silica-coated metal oxide sols obtained in Production Examples 16–20 and metal oxide particles derived from the five types of surface-hydrophobicized silica-coated metal oxide sols obtained in Production Examples 21–25 were used as test substances for measurement of the powder dynamic friction coefficient by the glass plate method.

Specifically, each test powder was dispersed onto a 100×200 mm glass plate at 10 mg/cm$^2$, and the glass plate was mounted on the test stand of a surface property measuring instrument (HEIDON), for measurement of the friction coefficient with a load of 22.2 g/cm$^2$, a moving speed of 200 mm/min. and a moving distance of 20 mm. The results are shown in Tables 5 and 6.

The surface-hydrophobicized silica-coated metal oxide particles and metal oxide powders derived from silica-coated metal oxide sols and surface-hydrophobicized silica-coated metal oxide sols according to the invention all had friction coefficients of 0.550 or smaller, thus exhibiting friction coefficients equivalent to that of conventional silica-coated metal oxide particles. The friction coefficients of the uncoated metal oxide particles and conventionally surface-treated titania particles were much larger than 0.550. That is, it may be concluded that even with hydrophobicizing treatment, there is no adverse effect on the low friction coefficients of conventional silica-coated surface-treated metal oxide particles. This also suggests that cosmetic materials comprising metal oxide particles derived from silica-coated metal oxide sols and metal oxide particles derived from surface-hydrophobicized silica-coated metal oxide sols according to the invention give an even more excellent feel during use than the prior art.

(Pigment Decoloration Rate Measurement: Sunset Yellow Method)

The five types of surface-hydrophobicized silica-coated metal oxide particles obtained in Production Examples 1b–5b and five types of silica-coated metal oxide particles obtained in Production Examples 1a–5a, four types of uncoated metal oxide particles corresponding to each of the four types of silica-coated metal oxide particles obtained in Production Examples 2–4 and 6, and two types of conventionally surface-treated titania particles (MT100T by Teika Co. and TTO-55A by Ishihara Sangyo) were used as test substances for measurement of the pigment decoloration rate by the Sunset Yellow method.

Also, the five types of silica-coated metal oxide sols obtained in Production Examples 6–10 and the five types of surface-hydrophobicized silica-coated metal oxide sols obtained in Production Examples 11–15 were used as test substances for measurement of the pigment decoloration rate by the Sunset Yellow method.

Specifically, the cosmetic pigment Sunset Yellow was dissolved in 98 wt % glycerin to a pigment concentration of 0.02 wt %. Each test substance was dispersed to 0.067 wt % and the dispersion was exposed to ultraviolet irradiation (ultraviolet ray intensity: 1.65 mW/cm$^2$). The absorbance at 490 nm which is the maximum absorption wavelength of Sunset Yellow with an optical path of 1 mm was periodically measured with a spectrophotometer (SHIMADZU UV-160), and the reduction rate in the absorbance ($\Delta A490/h$) was calculated. The results are also shown in Tables 5 and 6.

All of the surface-hydrophobicized silica-coated metal oxide particles and silica-coated metal oxide sols according to the invention had pigment decoloration rates of 0.060 ($\Delta A490/h$) or lower, thus exhibiting pigment decoloration rates equivalent to that of conventional silica-coated metal oxide particles. This was approximately 1/1000 with respect to the uncoated metal oxide particles and approximately 1/100 with respect to the conventionally surface-treated titania particles, and therefore the pigment decomposition was minimized.

Surface-hydrophobicized silica-coated metal oxide particles and silica-coated metal oxide sol-derived silica-coated metal oxide particles according to the invention clearly maintain the low pigment decomposition properties of conventional silica-coated metal oxide particles even after surface treatment with a hydrophobicizing agent, and can therefore provide cosmetic materials with high storage stability.

TABLE 5

Properties of metal oxide particles (2)

| Metal oxide particles | Ultraviolet absorber decomposition rate ($\Delta A340/h$) | Powder dynamic friction coefficient | Pigment decoloration rate ($\Delta A490/h$) |
|---|---|---|---|
| Prod. Ex. 1a | 0.001 | 0.487 | 0.018 |
| Prod. Ex. 2a | 0.001 | 0.403 | 0.006 |
| Prod. Ex. 3a | 0.002 | 0.428 | 0.013 |
| Prod. Ex. 4a | 0.002 | 0.413 | 0.008 |
| Prod. Ex. 5a | 0.001 | 0.456 | 0.009 |
| Prod. Ex. 1b | 0.001 | 0.490 | 0.019 |
| Prod. Ex. 2b | 0.001 | 0.408 | 0.008 |
| Prod. Ex. 3b | 0.002 | 0.432 | 0.012 |
| Prod. Ex. 4b | 0.002 | 0.425 | 0.010 |
| Prod. Ex. 5b | 0.001 | 0.478 | 0.011 |

TABLE 6

Properties of metal oxide sols (2)

| Metal oxide sol/powder | Photo-catalytic activity mmH$_2$O/min. | Ultraviolet absorber decomposition rate ($\Delta A340/h$) | Powder dynamic friction coefficient | Pigment decoloration rate ($\Delta A490/h$) |
|---|---|---|---|---|
| Prod. Ex. 6  | 48 | 0.001 | — | 0.019 |
| Prod. Ex. 7  | 41 | 0.001 | — | 0.006 |
| Prod. Ex. 8  | 38 | 0.002 | — | 0.009 |
| Prod. Ex. 9  | 37 | 0.002 | — | 0.010 |
| Prod. Ex. 10 | 37 | 0.001 | — | 0.009 |
| Prod. Ex. 11 | 46 | 0.001 | — | 0.013 |
| Prod. Ex. 12 | 40 | 0.001 | — | 0.006 |
| Prod. Ex. 13 | 35 | 0.001 | — | 0.008 |
| Prod. Ex. 14 | 36 | 0.001 | — | 0.009 |
| Prod. Ex. 15 | 36 | 0.001 | — | 0.009 |
| Prod. Ex. 16 | — | — | 0.465 | — |
| Prod. Ex. 17 | — | — | 0.398 | — |
| Prod. Ex. 18 | — | — | 0.402 | — |
| Prod. Ex. 19 | — | — | 0.401 | — |
| Prod. Ex. 20 | — | — | 0.465 | — |

TABLE 6-continued

Properties of metal oxide sols (2)

| Metal oxide sol/powder | Photo-catalytic activity mmH$_2$O/min. | Ultraviolet absorber decomposition rate (ΔA340/h) | Powder dynamic friction coefficient | Pigment decoloration rate (ΔA490/h) |
|---|---|---|---|---|
| Prod. Ex. 21 | — | 0.466 | — | — |
| Prod. Ex. 22 | — | 0.400 | — | — |
| Prod. Ex. 23 | — | 0.403 | — | — |
| Prod. Ex. 24 | — | 0.401 | — | — |
| Prod. Ex. 25 | 36 | 0.001 | 0.457 | 0.009 |

Cosmetic Examples 1–4

Combination Foundations

The four types of surface-hydrophobicized silica-coated metal oxide particles obtained in Production Examples 1b–4b were used to prepare combination foundations having the formulation listed below, according to an established method. All of the surface-hydrophobicized silica-coated metal oxide particles dispersed satisfactorily during the preparation.

Combination Foundation Formulation

Surface-hydrophobicized silica-coated metal oxide

| particles | 6.0 wt % |
|---|---|
| Silicone-treated talc | 19.0 wt % |
| Silicone-treated mica | 40.0 wt % |
| Silicone-treated iron oxide (red) | 1.0 wt % |
| Silicone-treated iron oxide (yellow) | 3.0 wt % |
| Silicone-treated iron oxide (black) | 0.3 wt % |
| Silicone-treated titania | 15.0 wt % |
| Zinc stearate | 0.2 wt % |
| Nylon powder | 2.0 wt % |
| Squalane | 4.0 wt % |
| Solid paraffin | 0.5 wt % |
| Dimethylpolysiloxane | 4.0 wt % |
| Glycerin triisooctanoate | 5.0 wt % |
| Antioxidant | q.s. |
| Preservative | q.s. |
| Aroma | q.s. |

Comparison Cosmetic Examples 1–4

Combination Foundations

In cosmetic examples 1–4, the conventional silica-coated metal oxide particles obtained in Production Examples 1a–4a were used instead of the surface-hydrophobicized silica-coated metal oxide particles, to prepare combination foundations.

The foundations of cosmetic examples 1–4 and comparison cosmetic examples 1–4 were subjected to an organoleptic test to evaluate the feel during use. The results are shown in Table 7. The foundations containing silica-coated metal oxide particles according to the invention all exhibited a satisfactory feel during use. On the other hand, an ordinary or less than ordinary feel during use was exhibited by the foundations containing uncoated metal oxide particles and conventionally surface-treated titania particles. A correlation was also found between the dynamic friction coefficients of the added metal oxide particles and the feel during use of the foundations.

TABLE 7

Feel during use of metal oxide particles

| Cosmetic material | Metal oxide particles | Feel during use |
|---|---|---|
| Comparison cosmetic example 1 | Prod. Ex. 1a | poor |
| Comparison cosmetic example 2 | Prod. Ex. 2a | fair |
| Comparison cosmetic example 3 | Prod. Ex. 3a | poor |
| Comparison cosmetic example 4 | Prod. Ex. 4a | fair |
| Cosmetic example 1 | Prod. Ex. 1b | good |
| Cosmetic example 2 | Prod. Ex. 2b | very good |
| Cosmetic example 3 | Prod. Ex. 3b | very good |
| Cosmetic example 4 | Prod. Ex. 4b | very good |

Cosmetic Examples 5–7

Foundations having the following formulation were prepared according to an established method. The three types of surface-hydrophobicized silica-coated metal oxide particles obtained in Production Examples 2b–4b were used as the surface-hydrophobicized silica-coated metal oxide particles. All of the surface-hydrophobicized silica-coated titania particles and other surface-hydrophobicized silica-coated metal oxide particles dispersed satisfactorily during the preparation.

Foundation Formulation

Surface-hydrophobicized silica-coated titania

| particles (Prod. Ex. 1b) | 10.0 wt % |
|---|---|
| Surface-hydrophobicized silica-coated metal oxide particles | 5.0 wt % |
| Talc | 17.8 wt % |
| Kaolin | 15.0 wt % |
| Zinc flower | 15.0 wt % |
| Iron oxide (red) | 1.0 wt % |
| Iron oxide (yellow) | 3.0 wt % |
| Iron oxide (black) | 0.2 wt % |
| Solid paraffin | 3.0 wt % |
| Microcrystalline wax | 6.0 wt % |
| Bees wax | 2.0 wt % |
| Vaseline | 12.0 wt % |
| Lanolin acetate | 1.0 wt % |
| Squalane | 6.0 wt % |
| Isopropyl palmitate | 18.0 wt % |
| Antioxidant | q.s. |
| Aroma | q.s. |

Upon organoleptic testing of the foundations, all of the foundations had a very satisfactory feel during use.

Cosmetic Example 8

W/O Emulsion Foundation

The surface-hydrophobicized silica-coated titania particles obtained in Production Example 1b were used to prepare a W/O emulsion foundation having the following formulation, according to an established method. The surface-hydrophobicized silica-coated titania particles satisfactorily dispersed during the preparation.

W/O Emulsion Foundation Formulation

Surface-hydrophobicized silica-coated titania

| particles (Prod. Ex. 1b) | 9.5 wt % |
|---|---|
| Sericite | 5.4 wt % |
| Kaolin | 4.0 wt % |
| Iron oxide (red) | 0.4 wt % |
| Iron oxide (black) | 0.2 wt % |
| Iron oxide (yellow) | 0.8 wt % |
| Liquid paraffin | 5.0 wt % |
| Decamethylcyclopentanedioxane | 12.0 wt % |
| Polyoxyethylene modified dimethylpolysiloxane | 4.0 wt % |
| 1,3 butyleneglycol | 5.0 wt % |
| Purified water | 51.6 wt % |
| Dispersing agent | 0.1 wt % |
| Stabilizer | 2.0 wt % |
| Preservative | q.s. |
| Aroma | q.s. |

Upon organoleptic testing, the foundation had a very satisfactory feel during use.

Cosmetic Example 9

Anti-sunburn Cream

The surface-hydrophobicized silica-coated titania particles obtained in Production Example 1b were used to prepare an anti-sunburn cream having the following formulation, according to an established method. The surface-hydrophobicized silica-coated titania particles satisfactorily dispersed during the preparation

Anti-sunburn Cream Formulation

Surface-hydrophobicized silica-coated titania

| particles (Prod. Ex. 1b) | 5.0 wt % |
|---|---|
| Octyl paramethoxycinnamate | 5.0 wt % |
| Oxybenzone | 3.0 wt % |
| 4-tertbutyl-4'-methoxybenzoylmethane | 1.0 wt % |
| Squalane | 39.0 wt % |
| Glycerin diisostearate | 3.0 wt % |
| Liquid paraffin | 10.0 wt % |
| Organic modified montmorillonite | 1.5 wt % |
| 1,3-butyleneglycol | 5.0 wt % |
| Purified water | 37.5 wt % |
| Aroma | q.s. |
| Preservative | q.s. |

Upon organoleptic testing, the anti-sunburn cream had a very satisfactory feel during use.

Cosmetic Example 10

Sunoil

The surface-hydrophobicized silica-coated zinc oxide particles obtained in Production Example 2b were used to prepare a sunoil having the following formulation, according to an established method. The surface-hydrophobicized silica-coated zinc oxide particles satisfactorily dispersed during the preparation.

Sunoil Formulation

Surface-hydrophobicized silica-coated zinc oxide

| particles (Prod. Ex. 2b) | 1.0 wt % |
|---|---|
| Isopropyl paramethoxycinnamate | 0.5 wt % |
| Liquid paraffin | 56.5 wt % |
| Isopropyl myristate | 10.0 wt % |
| Silicone oil | 30.0 wt % |
| Silicone resin | 2.0 wt % |
| Aroma | q.s. |
| Antioxidant | q.s. |

Upon organoleptic testing, the sunoil had a very satisfactory feel during use.

Cosmetic Example 11

W/O Emulsion

The surface-hydrophobicized silica-coated titania particles obtained in Production Example 1b were used to prepare an emulsion having the following formulation, according to an established method. The surface-hydrophobicized silica-coated titania particles satisfactorily dispersed during the preparation.

Emulsion Formulation

Surface-hydrophobicized silica-coated titania

| particles (Prod. Ex. 1b) | 3.0 wt % |
|---|---|
| Microcrystalline wax | 1.0 wt % |
| Bees wax | 2.0 wt % |
| Lanolin | 2.0 wt % |
| Liquid paraffin | 18.0 wt % |
| Squalane | 10.0 wt % |
| Polyoxyethylenesorbitan fatty acid ester | 1.0 wt % |
| Sorbitan sesquioleic acid ester | 4.0 wt % |
| Propyleneglycol | 7.0 wt % |
| Purified water | 52.0 wt % |
| Aroma | q.s. |
| Preservative | q.s. |

Upon organoleptic testing, the emulsion had a very satisfactory feel during use.

Cosmetic Example 12

W/O Cream

The surface-hydrophobicized silica-coated titania particles obtained in Production Example 1b were used to prepare a cream having the following formulation, according to an established method. The surface-hydrophobicized silica-coated titania particles satisfactorily dispersed during the preparation.

W/O Cream Formulation

Surface-hydrophobicized silica-coated titania

| particles (Prod. Ex. 1b) | 7.0 wt % |
|---|---|
| Microcrystalline wax | 8.5 wt % |
| Solid paraffin | 2.0 wt % |
| Bees wax | 3.0 wt % |
| Vaseline | 5.0 wt % |

| -continued | |
|---|---|
| Reduced lanolin | 5.0 wt % |
| Squalane | 30.0 wt % |
| Hexadecyladipic acid ester | 10.0 wt % |
| Glycerin monooleate | 3.5 wt % |
| Polyoxyethylenesorbitan monooleic acid ester | 1.0 wt % |
| Propylene glycol | 5.0 wt % |
| Purified water | 20.0 wt % |
| Aroma | q.s. |
| Antioxidant | q.s. |
| Preservative | q.s. |

Upon organoleptic testing, the cream had a very satisfactory feel during use

Cosmetic Example 13

Cream

The surface-hydrophobicized silica-coated titania particles obtained in Production Example 1b and the surface-hydrophobicized silica-coated zinc oxide particles obtained in Production Example 2b were used to prepare a cream having the following formulation, according to an established method. The surface-hydrophobicized silica-coated titania particles and the surface-hydrophobicized silica-coated zinc oxide particles obtained in Production example 2b satisfactorily dispersed during the preparation.

Cream Formulation

Surface-hydrophobicized silica-coated titania

| particles (Prod. Ex. 1) | 7.0 wt % |
|---|---|
| Surface-hydrophobicized silica-coated zinc oxide particles (Prod. Ex. 2) | 7.0 wt % |
| Squalane | 17.0 wt % |
| Cetyl isooctanoate | 7.5 wt % |
| Microcrystalline wax | 1.0 wt % |
| Organic modified montmorillonite | 1.3 wt % |
| Polyoxyethyleneglycerol triisostearic acid ester | 0.2 wt % |
| Glycerin | 8.5 wt % |
| Purified water | 50.5 wt % |
| Aroma | q.s. |
| Preservative | q.s. |

Upon organoleptic testing, the cream had a very satisfactory feel during use.

Cosmetic Example 14

Oil-based Cream

The surface-hydrophobicized silica-coated titania particles obtained in Production Example 1b were used to prepare a cream having the following formulation, according to an established method. The surface-hydrophobicized silica-coated titania particles satisfactorily dispersed during the preparation.

Oil-based Cream Formulation

Surface-hydrophobicized silica-coated titania

| particles (Prod. Ex. 1b) | 5.0 wt % |
|---|---|
| Ceresin | 7.5 wt % |
| Microcrystalline wax | 5.0 wt % |

| -continued | |
|---|---|
| Vaseline | 33.0 wt % |
| Liquid paraffin | 47.5 wt % |
| Low-molecular polyethylene | 2.0 wt % |
| Aroma | q.s. |

Upon organoleptic testing, the cream had a very satisfactory feel during use.

Cosmetic Example 15

Pack

The surface-hydrophobicized silica-coated titania particles obtained in Production Example 1b were used to prepare a pack having the following formulation, according to an established method. The surface-hydrophobicized silica-coated titania particles satisfactorily dispersed during the preparation.

Pack Formulation

Surface-hydrophobicized silica-coated titania

| particles (Prod. Ex. 1b) | 5.0 wt % |
|---|---|
| Talc | 10.0 wt % |
| Polyvinyl acetate emulsion | 15.0 wt % |
| Polyvinyl alcohol | 10.0 wt % |
| Sorbitol | 5.0 wt % |
| PEG 400 | 5.0 wt % |
| Jojoba oil | 2.9 wt % |
| Squalane | 2.0 wt % |
| Polyoxyethylenesorbitan monostearic acid ester | 1.0 wt % |
| Ethyl alcohol | 8.0 wt % |
| Purified water | 37.7 wt % |
| Aroma | q.s. |
| Preservative | q.s. |

Upon organoleptic testing, the pack had a very satisfactory feel during use.

Cosmetic Example 16

Lipstick

The surface-hydrophobicized silica-coated titania particles obtained in Production Example 1b were used to prepare a lipstick having the following formulation, according to an established method. The surface-hydrophobicized silica-coated titania particles satisfactorily dispersed during the preparation.

Lipstick Formulation

Surface-hydrophobicized silica-coated titania

| particles (Prod. Ex. 1b) | 4.5 wt % |
|---|---|
| Castor oil | 30.0 wt % |
| Ceresin | 4.0 wt % |
| Candelilla wax | 8.0 wt % |
| Carnauba wax | 2.0 wt % |
| Propylene glycol | 1.0 wt % |
| Glycerin | 2.0 wt % |
| Isostearic diglyceride | 40.0 wt % |
| Polyoxyethylene/polyoxypropylene-2-tetradecyl ether | 1.0 wt % |
| Red colorant | 2.5 wt % |
| Purified water | 5.0 wt % |
| Aroma | q.s. |
| Antioxidant | q.s. |

Upon organoleptic testing, the lipstick had a very satisfactory feel during use.

Cosmetic Examples 17–20

Foundations for Organoleptic Test

Foundations were prepared having the following formulation, according to a common method. The test substances used were the four types of silica-coated metal oxide particles obtained in Production Examples 1b–4b.

Foundation Formulation for Organoleptic Test

| | |
|---|---|
| Test substance | 6.0 wt % |
| Silicone-treated talc | 18.0 wt % |
| Silicone-treated mica | 39.0 wt % |
| Silicone-treated iron oxide (red) | 1.0 wt % |
| Silicone-treated iron oxide (yellow) | 3.0 wt % |
| Silicone-treated iron oxide (black) | 0.3 wt % |
| Silicone-treated titania | 15.0 wt % |
| Zinc stearate | 0.2 wt % |
| Nylon powder | 2.0 wt % |
| Squalane | 4.0 wt % |
| Solid paraffin | 0.5 wt % |
| Dimethylpolysiloxane | 4.0 wt % |
| Glycerin triisooctanoate | 5.0 wt % |
| Antioxidant mixture | 2.0 wt % |
| Preservative | q.s. |
| Aroma | q.s. |

AS the antioxidant mixture there was used a mixture of 5% β-carotene, 5% astaxanthin, 20% magnesium L-ascorbate-2-phosphate, 10% sodium L-ascorbate-2-phosphate, 10% L-ascorbate-2-glucoside, 10% 5,6-benzylidene L-ascorbate-2-phosphate, 10% natural vitamin E, 5% dl-α-tocopherol, 5% dl-α-tocopheryl acetic acid ester, 5% sodium dl-α-tocopherylphosphate, 5% citric acid, 5% phosphoric acid and 5% epigallocatechin (proportions in percent by weight).

Comparison Cosmetic Examples 5–8

Foundations for Organoleptic Test

The test substances used were foundations having the same formulation as cosmetic examples 17–20, except that the four types of silica-coated metal oxide particles obtained in Production Examples 1a–4a were used.

(Organoleptic Test)

The feel during use of the foundations prepared in cosmetic examples 17–20 and comparison cosmetic examples 5–8 was evaluated by an organoleptic test with 50 female evaluators between age 20 and 49. The feel during use of each foundation was assigned points by each of the 50 evaluators based on the following scale:

Very good: 5

Good: 3

Fair: 2

Poor: 1

Very poor: 0

Next, the evaluation points from the 50 evaluators were totaled to determine the feel during use on the following 5-level scale.

| | |
|---|---|
| 250–200: very good | (++) |
| 200–150: good | (+) |
| 150–100: fair | (+−) |
| 100–50: poor | (−) |
| 50–0: very poor | (−−) |

The results are shown in Table 8. The feel during use of the foundations containing the silica-coated metal oxide particles according to the invention were all very good (++). On the other hand, the foundations containing the conventional silica-coated metal oxide particles were given an evaluation of fair (+−).

TABLE 8

Results of organoleptic test

| Sample | Metal oxide particles used | Evaluation |
|---|---|---|
| Cosmetic ex. 17 | Surface-hydrophobicized silica-coated titania particles (Prod. Ex. 1b) | ++ |
| Cosmetic ex. 18 | Surface-hydrophobicized silica-coated zinc oxide particles (Prod. Ex. 2b) | ++ |
| Cosmetic ex. 19 | Surface-hydrophobicized silica-coated cerium oxide particles (Prod. Ex. 3b) | ++ |
| Cosmetic ex. 20 | Surface-hydrophobicized silica-coated zirconium particles (Prod. Ex. 4b) | ++ |
| Comp. cosm. ex. 5 | Silica-coated titania particles (Prod. Ex. 1a) | − |
| Comp. cosm. ex. 6 | Silica-coated zinc oxide particles (Prod. Ex. 2a) | +− |
| Comp. cosm. ex. 7 | Silica-coated cerium oxide particles (Prod. Ex. 3a) | − |
| Comp. cosm. ex. 8 | Silica-coated zirconium particles (Prod. Ex. 4a) | +− |

Production examples for surface-hydrophobicized silica-coated metal oxides according to the invention will now be further explained.

Cosmetic Examples 21–28

Surface-hydrophobicized silica-coated titania particles were obtained under the same preparation conditions as in Production Example 1b, except that the alkylalkoxysilanes listed in Table 9 were used instead of dimethyldiethoxysilane.

TABLE 9

| Example No. | Alkylalkoxysilane | Secondary particle size μm | Light transmittance Abs360/ Abs530 | Water repellency | Powder dynamic friction coefficient |
|---|---|---|---|---|---|
| 21 | Dimethyldimethoxysilane | 1.5 | 2.9 | + | 0.48 |
| 22 | Diethyldiethoxysilane | 1.9 | 2.5 | + | 0.49 |
| 23 | Diphenyldiethoxysilane | 1.9 | 2.4 | + | 0.50 |
| 24 | Methyltriethoxysilane | 1.9 | 2.3 | + | 0.50 |
| 25 | Phenyltriethoxysilane | 1.6 | 2.5 | + | 0.50 |
| 26 | Phenyldiethoxysilane | 1.8 | 2.5 | + | 0.49 |
| 27 | Methyldiethoxysilane | 1.8 | 2.7 | + | 0.48 |
| 28 | Methylethyldimethoxysilane | 1.9 | 2.8 | + | 0.49 |

Cosmetic Examples 29–36

The silica-coated metal oxide particles obtained in Production Examples 1a–5a were surface-treated by a dry method. Specifically, 100 g of the silica-coated metal oxide particles was placed in a Henschel stirring mixer (LFS-GS-1J, product of Fukae Kogyo Co.), and the hydrophobicizing agents listed in Table 10 or their solutions were sprayed in an amount corresponding to 10 wt % of the metal oxide particles while rotating the mixer at 3000 rpm to uniformly adhere them onto the surfaces of the silica-coated metal oxide particles, after which drying was carried out at 80–105° C. The results are shown in Table 10.

TABLE 10

| Example No. | Metal oxide particles (starting material) | Hydrophobicizing agent | Secondary particle size μm | Light transmittance A360/ A530 | Water repellency | Powder dynamic friction coefficient |
|---|---|---|---|---|---|---|
| 29 | Prod. Ex. 1a | Dimethyldichlorosilane | 1.7 | 2.9 | + | 0.48 |
| 30 | Prod. Ex. 2a | Dimethyldiethoxysilane | 2.3 | 2.5 | + | 0.49 |
| 31 | Prod. Ex. 3a | Hexamethyldisilazane | 3.9 | 2.4 | + | 0.50 |
| 32 | Prod. Ex. 4a | Diphenylpolysiloxane | 2.9 | 2.3 | + | 0.50 |
| 33 | Prod. Ex. 5a | γ-aminopropyl triethoxysilane | 3.6 | 2.5 | + | 0.50 |
| 34 | Prod. Ex. 1a | Dimethylpolysiloxane | 3.2 | 2.6 | + | 0.49 |
| 35 | Prod. Ex. 1a | Magnesium stearate | 3.5 | 2.5 | + | 0.50 |
| 36 | Prod. Ex. 1a | Vinyltrimethoxysilane | 3.0 | 2.6 | + | 0.51 |

Cosmetic Examples 37–39

Anti-sunburn Emulsions

Anti-sunburn emulsions were prepared having the following formulation, by an established method. Specifically, polyethylene glycol was added to purified water, and after heating to dissolution, the test substance and Veegum were added and a homomixer was used to obtain a uniform dispersion which was kept at 70° C. (aqueous phase). The other components were added and the mixture was heated to dissolution and kept at 70° C. (oil phase). The oil phase was added to the aqueous phase and the mixture was emulsified and dispersed uniformly with a homomixer, and then cooled to 35° C. while mixing. The test substances used were the three types of silica-coated metal oxide sols prepared in Production Examples 6–8, adjusted to a solid portion of 10%.

Anti-sunburn Emulsion Formulation

| | |
|---|---|
| Test substance | 70.0 wt % |
| Stearic acid | 2.0 wt % |
| Cetyl alcohol | 1.0 wt % |
| Vaseline | 5.0 wt % |
| Silicone oil | 2.0 wt % |
| Liquid paraffin | 10.0 wt % |
| Glycerinmonostearic acid ester (self-emulsifying) | 1.0 wt % |
| Polyoxyethylene (25 mole) monooleic acid ester | 1.0 wt % |
| Polyethyleneglycol 1500 | 5.0 wt % |

-continued

| | |
|---|---|
| Veegum | 0.5 wt % |
| Purified water | 2.2 wt % |
| Aroma | 0.1 wt % |
| Preservative | 0.2 wt % |

(Organoleptic Test)

The feel during use and finished transparent feel of the anti-sunburn emulsions prepared in cosmetic examples 37–39 were evaluated by an organoleptic test with 50 female evaluators between age 20 and 49. The feel during use of each sunburn emulsion was assigned points by each of the 50 evaluators based on the following scale:

Very good: 5

Good: 3

Fair: 2

Poor: 1

Very poor: 0

Next, the evaluation points from the 50 evaluators were totaled to determine the feel during use on the following 5-level scale.

|  |  |
|---|---|
| 250–200: very good | (++) |
| 200–150: good | (+) |
| 150–100: fair | (+−) |
| 100–50: poor | (−) |
| 50–0: very poor | (−−) |

The results are shown in Table 11. The feel during use and transparent feel of the sunburn emulsions containing the silica-coated metal oxide sols according to the invention were all very good (++). On the other hand, the anti-sunburn emulsions containing the conventional silica-coated metal oxide powder were given an evaluation of very good (++) or good (+) for the feel during use but an evaluation of fair (+−) or good (+) for the transparent feel.

Anti-sunburn emulsions containing silica-coated metal oxide sols according to the invention clearly exhibit particularly improved transparent feel compared to sunburn emulsions containing conventional silica-coated metal oxide powder.

TABLE 11

Results of organoleptic test (sunburn emulsions)

| Cosmetic example | Feel during use | Transparent feel |
|---|---|---|
| Cosmetic example 37 | very good (++) | very good (++) |
| Cosmetic example 38 | very good (++) | very good (++) |
| Cosmetic example 39 | very good (++) | very good (++) |

Cosmetic Examples 40–41

Foundations

Foundations were prepared having the following formulation, according to an established method. The test substances used were the two types of silica-coated metal oxide sol-derived silica-coated metal oxide particles obtained in Production Examples 16 and 17.

Foundation Formulation

|  |  |
|---|---|
| Test substance | 15.0 wt % |
| Mica | 15.0 wt % |
| Talc | 10.0 wt % |
| Zinc flower | 15.0 wt % |
| Iron oxide (red) | 1.5 wt % |
| Iron oxide (yellow) | 3.4 wt % |
| Glycerin | 10.0 wt % |
| Purified water | 30.0 wt % |
| Aroma | 0.1 wt % |

(Organoleptic Test)

The feel during use and finished transparent feel of the foundations prepared in cosmetic examples 40 and 41 were evaluated by an organoleptic test in the manner described above.

The results are shown in Table 12. The feel during use and transparent feel of the foundations containing the silica-coated metal oxide sol-derived metal oxide powders according to the invention were all very good (++). On the other hand, the foundations containing the conventional silica-coated metal oxide powders were given an evaluation of very good (++) or good (+) for the feel during use but an evaluation of fair (+−) or good (+) for the transparent feel.

Foundations containing silica-coated metal oxide sol-derived silica-coated metal oxide particles according to the invention clearly exhibit particularly improved transparent feel compared to foundations containing conventional silica-coated metal oxide powder.

TABLE 12

Results of organoleptic test (foundations)

| Cosmetic example | Feel during use | Transparent feel |
|---|---|---|
| Cosmetic example 40 | very good (++) | very good (++) |
| Cosmetic example 41 | very good (++) | very good (++) |

Cosmetic Examples 42–45

Foundations

Foundations were prepared having the following formulation, according to an established method. Each of the silica-coated metal oxide sols used was one of the four types of silica-coated metal oxide sol-derived silica-coated metal oxide powders obtained in Production Examples 17–20.

Foundation Formulation

Silica-coated titania sol-derived titania powder (Prod.

|  |  |
|---|---|
| Ex. 16) | 10.0 wt% |

Silica-coated metal oxide sol-derived silica-coated metal

|  |  |
|---|---|
| oxide particles | 5.0 wt% |
| Mica | 15.0 wt% |
| Talc | 10.0 wt% |
| Zinc flower | 15.0 wt% |
| Iron oxide red | 1.5 wt% |
| Iron oxide (yellow) | 3.5 wt% |
| Glycerin | 10.0 wt% |
| Purified water | 29.9 wt% |
| Aroma | 0.1 wt% |

Upon organoleptic testing of the above foundations, all of the foundations exhibited a very good feel during use and a very good transparent feel.

Cosmetic Example 46

Cosmetic Water

Cosmetic water was prepared having the following formulation, according to an established method.

Cosmetic Water Formulation

|  |  |
|---|---|
| Silica-coated zinc oxide sol (Prod. Ex. 7) | 30.0 wt% |
| Ethyl alcohol | 39.6 wt% |
| 1,3-butyleneglycol | 9.5 wt% |
| Castor oil | 4.9 wt% |
| Methyl paraben | 0.2 wt% |
| Purified water | 15.8 wt% |

Upon organoleptic testing of the above cosmetic water, an evaluation of good feel during use and very good transparent feel was received.

Cosmetic Example 47

Emulsion

An emulsion was prepared having the following formulation, according to an established method.

Emulsion Formulation

| | |
|---|---|
| Silica-coated titania sol (Prod. Ex. 6) | 30.0 wt% |
| Avocado Oil | 11.0 wt% |
| Behenyl alcohol | 0.6 wt% |
| Stearic acid | 0.4 wt% |
| Glycerin fatty acid ester | 0.9 wt% |
| Polyoxyethylene sorbitan fatty acid ester | 1.1 wt% |
| Polyoxyethylene alkyl ether | 0.4 wt% |
| 1,3-butyleneglycol | 10.1 wt% |
| Methyl paraben | 0.2 wt% |
| Aroma | 0.4 wt% |
| Purified water | 44.9 wt% |

Upon organoleptic testing of the above emulsion, an evaluation of very good feel during use and very good transparent feel was received.

Cosmetic Example 48

Cream

A cream was prepared having the following formulation, according to an established method.

Cream Formulation

| | |
|---|---|
| Silica-coated cerium oxide sol (Prod. Ex. 8) | 35.0 wt% |
| Squalane | 11.1 wt% |
| Stearic acid | 7.8 wt% |
| Stearyl alcohol | 6.0 wt% |
| Bees wax | 1.9 wt% |
| Propyleneglycol monostearate | 3.1 wt% |
| Polyoxyethylene cetyl ether | 1.1 wt% |
| 1,3-butyleneglycol | 11.9 wt% |
| Methyl paraben | 0.2 wt% |
| Aroma | 0.4 wt% |
| Purified water | 12.5 wt% |

Upon organoleptic testing of the above cream, an evaluation of good feel during use and very good transparent feel was received.

Cosmetic Example 49

Cream

A cream was prepared having the following formulation, according to an established method.

Cream Formulation

| | |
|---|---|
| Silica-coated zinc oxide sol (Prod. Ex. 7) | 35.0 wt% |
| Squalane | 15.2 wt% |
| Stearic acid | 7.8 wt% |
| Stearyl alcohol | 6.0 wt% |
| Bees wax | 1.9 wt% |
| Propyleneglycol monostearate | 3.1 wt% |
| Polyoxyethylene cetyl ether | 1.1 wt% |
| 1,3-butyleneglycol | 11.9 wt% |
| Methyl paraben | 0.2 wt% |
| Aroma | 0.4 wt% |
| Purified water | 10.4 wt% |

Upon organoleptic testing of the above cream, an evaluation of very good feel during use and very good transparent feel was received.

Cosmetic Example 50

Cream

A cream was prepared having the following formulation, according to an established method.

Cream Formulation

| | |
|---|---|
| Silica-coated zirconium oxide sol (Prod. Ex. 9) | 15.0 wt% |
| Squalane | 40.0 wt% |
| Glyceryl diisostearate | 3.0 wt% |
| Oxybenzene | 3.0 wt% |
| Organic modified montmorillonite | 1.5 wt% |
| 1,3-butyleneglycol | 5.0 wt% |
| Octyl p-methoxycinnamate | 5.0 wt% |
| 4-tertbutyl-4'-methoxydibenzoylmethane | 1.0 wt% |
| Methyl paraben | 0.2 wt% |
| Aroma | 0.4 wt% |
| Purified water | 25.9 wt% |

Upon organoleptic testing of the above cream, an evaluation of very good feel during use and transparent feel was received.

Cosmetic Example 51

Pack

A pack was prepared having the following formulation, according to an established method, using the silica-coated titania sol-derived titania powder obtained in Production Example 16 as the test substance.

Pack Formulation

| | |
|---|---|
| Test substance | 7.0 wt% |
| Polyvinyl alcohol | 14.5 wt% |
| Carboxymethylcellulose sodium | 4.8 wt% |
| 1,3-butyleneglycol | 2.9 wt% |
| Ethyl alcohol | 10.0 wt% |
| Methyl paraben | 0.1 wt% |
| Purified water | 60.7 wt% |

Upon organoleptic testing of the above pack, an evaluation of good feel during use and transparent feel was received.

Cosmetic Example 52

Lipstick

Lipstick was prepared having the following formulation, according to an established method, using as the test substance the surface-hydrophobicized silica-coated zinc oxide sol of Production Example 7, with silicone oil substituted as the medium.

Lipstick Formulation

| Test substance | 30.0 wt% |
|---|---|
| Castor oil | 18.3 wt% |
| Hexadecyl alcohol | 25.2 wt% |
| Lanolin | 3.9 wt% |
| Bees wax | 4.8 wt% |
| Ozokerite | 3.4 wt% |
| Candelilla wax | 6.2 wt% |
| Carnauba wax | 2.1 wt% |
| Methyl paraben | 0.1 wt% |
| Red pigment | 4.8 wt% |
| Aroma | 0.1 wt% |
| Purified water | 1.1 wt% |

Upon organoleptic testing of the above lipstick, an evaluation of very good feel during use and transparent feel was received.

Cosmetic Examples 53–57

Combination Foundation

Combination foundations were prepared having the following formulation and according to an established method, using as the test substances the five types of surface-hydrophobicized silica-coated metal oxide sol-derived silica-coated metal oxide particles obtained in Production Examples 21–25. All of the silica-coated metal oxide particles dispersed satisfactorily during the preparation.

Combination Foundation Formulation

| Test substance | 6.0 wt% |
|---|---|
| Silicone-treated talc | 19.0 wt% |
| Silicone-treated mica | 39.6 wt% |
| Silicone-treated iron oxide (red) | 1.0 wt% |
| Silicone-treated iron oxide (yellow) | 3.0 wt% |
| Silicone-treated iron oxide (black) | 0.3 wt% |
| Silicone-treated titania | 15.0 wt% |
| Zinc stearate | 0.2 wt% |
| Nylon powder | 2.0 wt% |
| Squalane | 4.0 wt% |
| Solid paraffin | 0.5 wt% |
| Dimethylpolysiloxane | 4.0 wt% |
| Glycerin triisooctanoate | 5.0 wt% |
| Antioxidant | 0.2 wt% |
| Preservative | 0.1 wt% |
| Aroma | 0.1 wt% |

The feel during use and transparent feel of the combination foundations prepared in cosmetic examples 53–57 were evaluated by an organoleptic test. The results are shown in Table 13. It was demonstrated that the foundations comprising surface-hydrophobicized silica-coated metal oxide sol-derived silica-coated metal oxide particles according to the invention all exhibit a very good feel during use and a very good transparent feel.

TABLE 13

Results of organoleptic test (combination foundations)

| Cosmetic example | Feel during use | Transparent feel |
|---|---|---|
| Cosmetic example 53 | very good (++) | very good (++) |
| Cosmetic example 54 | very good (++) | very good (++) |
| Cosmetic example 55 | very good (++) | very good (++) |
| Cosmetic example 56 | very good (++) | very good (++) |
| Cosmetic example 57 | very good (++) | very good (++) |

Cosmetic Example 58

Foundations

Foundations were prepared having the following formulation, according to an established method. The four types of surface-hydrophobicized silica-coated metal oxide sols obtained in Production Examples 17–20 were used as the surface-hydrophobicized silica-coated titania sol- and zinc oxide sol-derived silica-coated metal oxide particles obtained in each of Production Examples 21 and 22. All of the silica-coated titania particles and silica-coated zinc oxide particles dispersed satisfactorily during the preparation.

Foundation Formulation

Surface-hydrophobicized silica-coated titania sol-derived silica-coated titania particles (Prod. Ex. 21) 10.0 wt %
Surface-hydrophobicized silica-coated zinc oxide-derived silica-coated zinc oxide particles (Prod. Ex. 22) 5.0 wt %

| Talc | 17.5 wt% |
|---|---|
| Kaolin | 15.0 wt% |
| Zinc flower | 15.0 wt% |
| Iron oxide (red) | 1.0 wt% |
| Iron oxide (yellow) | 3.0 wt% |
| Iron oxide (black) | 0.2 wt% |
| Solid paraffin | 3.0 wt% |
| Microcrystalline wax | 6.0 wt% |
| Bees wax | 2.0 wt% |
| Vasaline | 12.0 wt% |
| Lanolin acetate | 1.0 wt% |
| Squalane | 6.0 wt% |
| Isopropyl palmitate | 18.0 wt% |
| Antioxidant | 0.2 wt% |
| Aroma | 0.1 wt% |

Upon organoleptic testing of the above foundations, all of the foundations received an evaluation of very good feel during use and very good transparent feel.

Cosmetic Example 59

W/O Emulsion Foundation

A W/O emulsion foundation was prepared having the following formulation, according to an established method, using the surface-hydrophobicized silica-coated titania sol obtained in Production Example 11.

W/O Emulsion Foundation Formulation

Surface-hydrophobicized silica-coated titania sol

| (Prod. Ex. 11) | 47.5 wt% |
|---|---|
| Sericite | 5.4 wt% |

-continued

| | |
|---|---|
| Kaolin | 4.0 wt% |
| Iron oxide (red) | 0.4 wt% |
| Iron oxide (black) | 0.2 wt% |
| Iron oxide (yellow) | 0.8 wt% |
| Liquid paraffin | 5.0 wt% |
| Decamethylcyclopentanedioxane | 12.0 wt% |
| Polyoxyethylene modified dimethylpolysiloxane | 4.0 wt% |
| 1,3-butyleneglycol | 5.0 wt% |
| Purified water | 13.3 wt% |
| Dispersing agent | 0.1 wt% |
| Stabilizer | 2.0 wt% |
| Preservative | 0.2 wt% |
| Aroma | 0.1 wt% |

Upon organoleptic testing of the above foundation, an evaluation of very good feel during use and very good transparent feel was received.

Industrial Applicability

According to the present invention there are provided cosmetic materials comprising surface-hydrophobicized silica-coated metal oxide particles obtained by using a hydrophobicizing agent for surface treatment of metal oxide particles coated with a silica film having a thickness of 0.1–100 nm, wherein the ratio I of the peak intensities of the infrared absorption spectrum at 1150–1250 cm$^{-1}$ and 1000–1100 cm$^{-1}$ ($I_1/I_2$: where $I_1$ is the absorption peak intensity at 1150–1250 cm$^{-1}$ and $I_2$ is the absorption peak intensity at 1000–1100 cm$^{-1}$) is 0.2 or greater, and the refractive index is 1.435 or greater, and having photocatalytic activity of no more than 60 Pa/min as measured by the tetralin autooxidation method. Such cosmetic materials exhibit satisfactory dispersion of the metal oxide particles in cosmetic bases, a high ultraviolet-screening function, a highly transparent feel for cosmetic finishing and excellent storage stability, and are therefore useful as practical cosmetic materials. The present invention also provides an economical production process for the silica-coated metal oxide sols, and further provides metal oxide sols with improved dispersing properties and transparency which are coated with dense, practical silica films, as well as ultraviolet-screening cosmetic materials with a particularly excellent transparent feel wherein the silica-coated metal oxide particles are satisfactorily dispersed.

What is claimed is:

1. A cosmetic material comprising silica-coated metal oxide particles coated with a hydrophobicizing agent in an amount sufficient to completely coat the surface of the silica-coated metal oxide particles and no more than 30 wt %, said silica-coated metal oxide particles having a silica film wherein the ratio I of the absorption peak intensities of the infrared absorption spectrum at 1150–1250 cm$^{-1}$ and 1000–1100 cm$^{-1}$ ($I=I_1/I_2$: where $I_1$ is the absorption peak intensity at 1150–1250cm$^{-1}$ and $I_2$ is the absorption peak intensity at 1000–1100 cm$^{-1}$) is 0.2 or greater, and the refractive index is 1.435 or greater.

2. A cosmetic material comprising surface-hydrophobicized silica-coated metal oxide particles according to claim 1, characterized in that the silica film thickness is 0.1–100 nm.

3. A cosmetic material according to claim 1 or 2, characterized in that the hydrophobicizing agent is one or more hydrophobicizing agents selected from the group consisting of silicone oils, organic alkoxysilanes and higher fatty acid salts.

4. A cosmetic material according to claim 1 or 2, characterized by comprising surface-hydrophobicized silica-coated metal oxide particles with a photocatalytic activity of no more than 60 Pa/min as measured by the tetralin autooxidation method.

5. A cosmetic material according to claim 1 or 2, characterized in that the surface-hydrophobicized silica-coated metal oxide particles have a primary particle size of 5–500 nm and a secondary particle size of 0.5–10 µm.

6. A cosmetic material according to claim 5, characterized in that the primary particle size of the surface-hydrophobicized silica-coated metal oxide particles is 5–120 nm and the silica film thickness is 0.5–25 nm.

7. A cosmetic material according to claim 1 or 2, characterized in that the metal oxide is one or more metal oxides selected from the group consisting of titanium oxide, zinc oxide, cerium oxide, zirconium oxide and iron oxide.

8. A cosmetic material according to claim 7, wherein the metal oxide is titanium oxide.

9. A cosmetic material according to claim 7, wherein the metal oxide is zinc oxide.

10. A cosmetic material according to claim 7, wherein the metal oxide is cerium oxide.

11. A cosmetic material according to claim 1 or 2, characterized by comprising an antioxidant in addition to the surface-hydrophobicized silica-coated metal oxide particles.

12. A cosmetic material according to claim 1 or 2, characterized by comprising an organic-based ultraviolet absorber in addition to the surface-hydrophobicized silica-coated metal oxide particles.

13. A cosmetic material characterized by comprising a silica-coated metal oxide sol obtained by a process for production of a silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, and/or a surface-hydrophobicized silica-coated metal oxide sol obtained by a process for production of a surface-hydrophobicized silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent.

14. A cosmetic material characterized by comprising silica-coated metal oxide particles obtained by solid/liquid separation, drying and, if necessary, pulverization of a silica-coated metal oxide sol obtained by a process for production of a silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of.0.11–10 and a silicon content in the range of 0.0001–5 moles/liter after combining, and depositing silica on the surface of the metal oxide sol particles to form a silica film, and surface-hydrophobicized silica-coated metal oxide particles obtained by solid/liquid separation, drying and if necessary pulverization of a surface-hydrophobicized silica-coated metal oxide sol obtained by a process for production of a surface-hydrophobicized silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water/organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coated metal oxide particles with a hydrophobicizing agent in an amount sufficient to completely coat the surface of the silica-coated metal oxide particles and no more than 30 wt %.

15. A cosmetic material characterized by comprising surface-hydrophobicized silica-coated metal oxide particles obtained by solid/liquid separation, drying and if necessary pulverization of a surface-hydrophobicized silica-coated metal oxide sol obtained by a process for production of a surface-hydrophobicized silica-coated metal oxide sol characterized by adding a) silicic acid or a silicic acid-producing precursor, b) an alkali, c) an organic solvent and if necessary, d) water, irrespective of order, to a metal oxide sol produced by hydrolysis, for a water organic solvent ratio in the range of 0.1–10 and a silicon content in the range of 0.0001–5 moles/liter after combining, and depositing silica on the surface of the metal oxide sol particles to form a silica film, thereby fabricating a silica-coated metal oxide sol, and then further surface treating the silica-coating metal oxide particles with a hydrophobicizing agent in an amount sufficient to completely coat the surface of the silica-coated metal oxide particles and no more than 30 wt %.

16. A cosmetic material according to claims 13 or 14 or 15;

characterized in that the thickness of the silica film of the metal oxide particles in the silica-coated metal oxide sol and surface-hydrophobicized silica-coated metal oxide sol is 0.1–25 nm.

17. A cosmetic material according to claim 13 or 14 or 15;

characterized in that the average primary particle size of the metal oxide particles in the silica-coated metal oxide sol and surface-hydrophobicized silica-coated metal oxide sol is 1–100 nm.

18. A cosmetic material according to claims 13 or 14 or 15;

characterized in that the photocatalytic activity of the metal oxide particles in the silica-coated metal oxide sol and surface-hydrophobicized silica-coated metal oxide sol is no more than 60 Pa/min as measured by the tetralin autooxidation method.

19. A cosmetic material according to claim 13, characterized in that the metal oxide is one or more metal oxides selected from the group consisting of titanium oxide, zinc oxide, cerium oxide, zirconium oxide and iron oxide.

20. A cosmetic material according to claim 13, characterized by comprising an antioxidant.

21. A cosmetic material according to claim 13, characterized by comprising an organic-based ultraviolet absorber.

22. A cosmetic material according to claim 13, wherein the cosmetic material comprises the silica-coated metal oxide sol, characterized in that for the silica film the ratio I of the absorption peak intensities of the infrared absorption spectrum at 1150–1250 $cm^{-1}$ and 1000–1100 $cm^{-1}$ ($I=I_1/I_2$: where $I_1$ is the maximum absorption peak intensity at 1150–1250 $cm^{-1}$ and $I_2$ is the maximum absorption peak intensity at 1000–1100 $cm^{-1}$) is 0.2 or more, and the refractive index is 1.435 or more.

23. A cosmetic material according to claim 13, wherein the cosmetic material comprises the surface-hydrophobicized silica-coated metal oxide sol, characterized in that for the silica film, the ratio I of the absorption peak intensities of the infrared absorption spectrum at 1150–1250 $cm^{-1}$ and 1000–1100 $cm^{-1}$ ($I=I_1/I_2$: where $I_1$ is the maximum absorption peak intensity at 1150–1250 $cm^{-1}$ and $I_2$ is the maximum absorption peak intensity at 1000–1100 $cm^{-1}$) is 0.2 or greater, and the refractive index is 1.435 or more.

24. A cosmetic material according to claim 15;

wherein the surface-hydrophobicized silica-coated metal oxide particles are obtained by using a hydrophobicizing agent for further surface treatment of metal oxide particles coated with a silica film wherein the ratio I of the absorption peak intensities of the infrared absorption spectrum at 1150–1250 $cm^{-1}$ and 1000–1100 $cm^{-1}$ ($I=I_1/I_2$: where $I_1$ is the absorption peak intensity at 1150–1250 $cm^{-1}$ and $I_2$ is the absorption peak intensity at 1000–1100 $cm^{-1}$) is 0.2 or more, and the refractive index is 1.435 or more.

25. A cosmetic material according to claim 13, characterized in that the thickness of the silica film of the metal oxide particles in the silica-coated metal oxide sol and surface-hydrophobicized silica-coated metal oxide sol is 0.1–25 nm.

26. A cosmetic material according to claim 13, characterized in that the average primary particle size of the metal oxide particles in the silica-coated metal oxide sol and surface-hydrophobicized silica-coated metal oxide sol is 1–100 nm.

27. A cosmetic material according to claim 13, characterized in that the photocatalytic activity of the metal oxide particles in the silica-coated metal oxide sol and surface-hydrophobicized silica-coated metal oxide sol is no more than 60 Pa/min as measured by the tetralin autooxidation method.

28. A cosmetic material according to claim 15, characterized in that the metal oxide is one or more metal oxides selected from the group consisting of titanium oxide, zinc oxide, cerium oxide, zirconium oxide and iron oxide.

29. A cosmetic material according to claim 15, characterized by comprising an antioxidant.

30. A cosmetic material according to claim 15, characterized by comprising an organic-based ultraviolet absorber.

* * * * *